United States Patent
Breneman et al.

(10) Patent No.: US 8,361,755 B2
(45) Date of Patent: Jan. 29, 2013

(54) COMPOSITIONS AND METHODS FOR GRAIN PROCESSING WITHOUT PH ADJUSTMENT

(75) Inventors: Suzanne Breneman, Orfordville, WI (US); Thomas S. Green, Cedar Rapids, IA (US); Michael Jay Pepsin, Castro Valley, CA (US); Vivek Sharma, North Liberty, IA (US); Jayarama K. Shetty, Pleasanton, CA (US)

(73) Assignee: Danisco US Inc., Palo Alto, CA (US)

( * ) Notice: Subject to any disclaimer, the term of this patent is extended or adjusted under 35 U.S.C. 154(b) by 116 days.

(21) Appl. No.: 12/753,811

(22) Filed: Apr. 2, 2010

(65) Prior Publication Data
US 2011/0020880 A1 Jan. 27, 2011

Related U.S. Application Data

(60) Provisional application No. 61/170,531, filed on Apr. 17, 2009.

(51) Int. Cl.
*C12P 19/14* (2006.01)
*C12N 9/00* (2006.01)
*C12N 9/90* (2006.01)
*C12N 1/20* (2006.01)
*C07H 21/04* (2006.01)

(52) U.S. Cl. ....... 435/99; 435/183; 435/252.3; 536/23.2

(58) Field of Classification Search ........................ None
See application file for complete search history.

(56) References Cited

U.S. PATENT DOCUMENTS

| 4,914,029 | A | 4/1990 | Caransa et al. |
| 5,756,714 | A | 5/1998 | Antrim et al. |
| 2005/0272137 | A1 | 12/2005 | Veit et al. |

FOREIGN PATENT DOCUMENTS

| EP | 0 380 343 | 8/1990 |
| WO | WO 98/11788 | 3/1998 |
| WO | WO 2006/043178 | 4/2006 |
| WO | WO 2008/097619 | 8/2008 |
| WO | WO 2008/097620 | 8/2008 |
| WO | WO 2009/100179 | 8/2009 |
| WO | WO 2009/129489 | 10/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Shetty, J., et al., "New liquefaction enzyme system for fuel ethanol." 2007 Fuel Ethanol Workshop & Expo., St. Louis, MO, Jun. 26, 2007.
International Search Report and the Written Opinion of the International Searching Authority for International Application No. PCT/US2010/028797, dated Oct. 19, 2010.

* cited by examiner

*Primary Examiner* — Christian Fronda
(74) *Attorney, Agent, or Firm* — Danisco US Inc.

(57) ABSTRACT

Described are compositions and methods relating to starch processing without a phytase pretreatment step and without adjustment of the slurry pH adjustment.

10 Claims, 6 Drawing Sheets

|                     |       | 1                                                    50 |
|---|---|---|
| (SEQ ID NO: 3) BP-110 | (1)   | NDTPASGYQVEKVVILSRHGVRAPTKMTQTMRDVTPYTWPEWPVKLGYIT |
| (SEQ ID NO: 5) BP-112 | (1)   | NDTPASGYQVEKVVILSRHGVRAPTKMTQTMRDVTPYTWPEWPVKLGYIT |
| (SEQ ID NO: 4) BP-111 | (1)   | NDTPASGYQVEKVVILSRHGVRAPTKMTQTMRDVTPYTWPEWPVKLGYIT |
| (SEQ ID NO: 2) BP-17  | (1)   | NDTPASGYQVEKVVILSRHGVRAPTKMTQTMRDVTPNTWPEWPVKLGYIT |
| (SEQ ID NO: 1) WT     | (1)   | NDTPASGYQVEKVVILSRHGVRAPTKMTQTMRDVTPNTWPEWPVKLGYIT |

|                     |       | 51                                                  100 |
|---|---|---|
| BP-110              | (51)  | PRGEHLISLMGGFYRQKFQQQGILSQSSCPTPNSIYVWTDVAQRTLKTGE |
| BP-112              | (51)  | PRGEHLISLMGGFYRQKFQQQGILPQGSCPTPNSIYVWTDVAQRTLKTGE |
| BP-111              | (51)  | PRGEHLISLMGGFYRQKFQQQGILPRGSCPTPNSIYVWTDVAQRTLKTGE |
| BP-17               | (51)  | PRGEHLISLMGGFYRQKFQQQGILSQGSCPTPNSIYVWTDVAQRTLKTGE |
| Buttiauxella-WT     | (51)  | PRGEHLISLMGGFYRQKFQQQGILSQGSCPTPNSIYVWADVDQRTLKTGE |

|                     |       | 101                                                 150 |
|---|---|---|
| BP-110              | (101) | AFLAGLAPQCGLTIHHQQNLEKADPLFHPVKAGICSMDKTQVQQAVEKEA |
| BP-112              | (101) | AFLAGLAPQCGLTIHHQQNLEKADPLFHPVKAGICSMDKTQVQQAVEKEA |
| BP-111              | (101) | AFLAGLAPQCGLTIHHQQNLEKADPLFHPVKAGICSMDKTQVQQAVEKEA |
| BP-17               | (101) | AFLAGLAPQCGLTIHHQQNLEKADPLFHPVKAGICSMDKTQVQQAVEKEA |
| Buttiauxella-WT     | (101) | AFLAGLAPQCGLTIHHQQNLEKADPLFHPVKAGTCSMDKTQVQQAVEKEA |

|                     |       | 151                                                 200 |
|---|---|---|
| BP-110              | (151) | QTPIDNLNQRYIPELALMNTVLNFSKSPWCQKHSADKPCDLALSMPSRLS |
| BP-112              | (151) | QTPIDNLNQRYIPELALMNTVLNFSKSPWCQKHSADKPCDLALSMPSRLS |
| BP-111              | (151) | QTPIDNLNQRYIPELALMNTILNFSKSPWCQKHSADKPCDLALSMPSKLS |
| BP-17               | (151) | QTPIDNLNQHYIPSLALMNTTLNFSKSPWCQKHSADKSCDLGLSMPSKLS |
| Buttiauxella-WT     | (151) | QTPIDNLNQHYIPFLALMNTTLNFSTSAWCQKHSADKSCDLGLSMPSKLS |

|                     |       | 201                                                 250 |
|---|---|---|
| BP-110              | (201) | IKDNGNEVSLDGAIGLSSTLAEIFLLEYAQGMPQAAWGNIHSEQEWALLL |
| BP-112              | (201) | IKDNGNEVSLDGAIGLSSTLAEIFLLEYAQGMPQAAWGNIHSEQEWALLL |
| BP-111              | (201) | IKDNGNEVSLDGAIGLSSTLAEIFLLEYAQGMPQVAWGNIHSEQEWALLL |
| BP-17               | (201) | IKDNGNEVSLDGAIGLSSTLAEIFLLEYAQGMPQAAWGNIHSEQEWALLL |
| Buttiauxella-WT     | (201) | IKDNGNKVALDGAIGLSSTLAEIFLLEYAQGMPQAAWGNIHSEQEWASLL |

|                     |       | 251                                                 300 |
|---|---|---|
| BP-110              | (251) | KLHNVYFDLMERTPYIARHKGTPLLQAISNALNPNATESKLPDISPDNKI |
| BP-112              | (251) | KLHNVYFDLMERTPYIARHKGTPLLQAISNALNPNATESKLPDISPDNKI |
| BP-111              | (251) | KLHNVYFDLMERTPYIARHKGTPLLQAISNALNPNATESKLPDISPDNKI |
| BP-17               | (251) | KLHNVYFDLMERTPYIARHKGTPLLQAISNALNPNATESKLPDISPDNKI |
| Buttiauxella-WT     | (251) | KLHNVQFDLMARTPYIARHNGTPLLQAISNALNPNATESKLPDISPDNKI |

|                     |       | 301                                                 350 |
|---|---|---|
| BP-110              | (301) | LFIAGHDTNIANIAGMLNMRWTLPGQPDNTPPGGALVFERLADKSGKQYV |
| BP-112              | (301) | LFIAGHDTNIANIAGMLNMRWTLPGQPDNTPPGGALVFERLADKSGKQYV |
| BP-111              | (301) | LFIAGHDTNIANIAGMLNMRWTLPGQPDNTPPGGALVFERLADKSGKQYV |
| BP-17               | (301) | LFIAGHDTNIANIAGMLNMRWTLPGQPDNTPPGGALVFERLADKSGKQYV |
| Buttiauxella-WT     | (301) | LFIAGHDTNIANIAGMLNMRWTLPGQPDNTPPGGALVFERLADKSGKQYV |

|                     |       | 351                                                 400 |
|---|---|---|
| BP-110              | (351) | SVSMVYQTLEQLRSQTPLSLNQPPGSVQLKIPGCNDQTAEGYCPLSTFTR |
| BP-112              | (351) | SVSMVYQTLEQLRSQTPLSLNQPPGSVQLKIPGCNDQTAEGYCPLSTFTR |
| BP-111              | (351) | SVSMVYQTLEQLRSQTPLSLNQPPGSVQLKIPGCNDQTAEGYCPLSTFTR |
| BP-17               | (351) | SVSMVYQTLEQLRSQTPLSLNQPAGSVQLKIPGCNDQTAEGYCPLSTFTR |
| Buttiauxella-WT     | (351) | SVSMVYQTLEQLRSQTPLSLNQPAGSVQLKIPGCNDQTAEGYCPLSTFTR |

|                     |       | 401    413 |
|---|---|---|
| BP-110              | (401) | VVSQSVEPGCQLQ |
| BP-112              | (401) | VVSQSVEPGCQLQ |
| BP-111              | (401) | VVSQSVEPGCQLQ |
| BP-17               | (401) | VVSQSVEPGCQLQ |
| Buttiauxella-WT     | (401) | VVSQSVEPGCQLQ |

*FIG. 4*

COMPOSITIONS AND METHODS FOR GRAIN PROCESSING WITHOUT PH ADJUSTMENT

CROSS-REFERENCE

This application claims priority from U.S. Provisional patent application No. 61/170,531 filed Apr. 17, 2009 which is incorporated herein in its entirety.

TECHNICAL FIELD

The present compositions and methods relate to the processing of grain/cereal starch into soluble dextrins and to ethanol without the addition of alkali or acid for pH adjustment.

BACKGROUND

The dry mill ethanol production process primarily utilizes whole ground grain, e.g., corn or milo, or fractionated corn. In a typical dry milling process, the entire corn kernel or other starchy grain is first milled to a specific particle size (<1.0 mm) and then processed without further separating the various components of the grain. The milled grain is made into a slurry (25-40% dissolved solid (DS) grain) with hot cook water (>90° C.), and mixed well in a mix box. An initial dose of thermostable liquefying alpha amylase is added to the slurry in the mix box before the slurry is transferred to a primary liquefaction tank.

Then the pH of the partially gelatinized starch slurry is conventionally adjusted to greater than pH 5.8 using ammonia, and then incubated with a thermostable alpha amylase at 85-86° C. for 15-20 minutes before being sent through a jet cooker maintained at 105-108° C. for a holding time of 3-5 minutes. Following jet cooking, the gelatinized starch slurry is held in a cook tube at high pressure for 8 to 10 minutes to complete gelatinization, and then flashed to atmospheric pressure and maintained the temperature at about 85° C.

A second dose of thermostable alpha amylase is typically added to complete the liquefaction of starch as the slurry is held at the elevated temperature for 90 to 120 minutes and then sent to a series of heat exchangers for reducing the temperature to 32° C. prior to fermentation. The high temperature also reduces the high risk of microbial contamination of the mash. Following liquefaction, the pH of the mash is decreased to less than pH 5.2 using dilute sulfuric acid and then cooled to 32° C. prior to fermentation. This process is diagramed in FIG. 1, which indicates the steps where pH adjustments are necessary.

In a dry mill ethanol process, the whole ground grain is generally mixed with fresh water, condensate water, and thin stillage (generally called cook water or backset) at 10-50% to produce a mash with a DS content ranging from 25% to 45%. The natural pH of the whole ground grains, such as corn or milo/sorghum, in water ranges from 5.5 to 6.2 depending upon the length of storage of the grain and extent of microbial infection. However, the pH is lowered to pH 4.8 to pH 5.2 when the ground grains are mixed with varying amount of thin stillage. The pH of the thin stillage also varies significantly depending on the particular processing plant, with typical pH value ranging from 3.8 to 4.5. Some ethanol producers add acids, e.g., to lower the pH in the beer and to reduce the risk of microbial contamination prior to distillation, thereby lower the pH.

To illustrate this point, the effect on final pH of adding of thin stillage from a commercial ethanol plant at different ratios in the make-up water added to a whole ground corn slurry was recently studied at an ethanol production plant in Monroe, Wis., USA. As shown in Table 1, the more thin stillage that is used as make-up water, the lower the final pH of the slurry.

TABLE 1

Effect of thin stillage concentrations on the final pH of a whole ground corn slurry (32% DS corn), stirred for 2 hours at 32° C. (155° F.).

| Thin stillage, (% w/w) | Final pH of 32% DS whole ground corn slurry |
|---|---|
| 0 | 5.52 |
| 20 | 5.29 |
| 40 | 5.16 |
| 50 | 5.09 |
| 60 | 5.05 |
| 80 | 4.98 |
| 100 | 4.94 |

It is generally important for ethanol production plants to use cook water as make-up water in the slurry tank to conserve water; therefore this practice should not necessarily be discouraged. However, current commercially-available thermostable alpha amylase enzymes that are used to convert granular starch in whole ground grains into soluble dextrins during primary liquefaction are not stable below pH 5.6 at the elevated temperatures used in the process. Providing a suitable environment for the alpha amylases, therefore, necessitates the adjustment of the pH to pH 5.8 to pH 6.0 using suitable alkali reagents, such as sodium hydroxide, sodium carbonate, or ammonia. This pH adjustment is more than just an added step because it typically adds a significant amount of ions, e.g., sodium to the fermentation medium, which may impact the growth of microorganisms during subsequent processing steps, e.g., the growth of yeast during fermentation.

Starting the yeast fermentation at a higher pH due to the addition of alkaline reagents increases the risk of microbial contamination. As a result, alcohol producers generally reduce the pH after liquefaction to less than pH 5.0 (e.g., pH 4.2 to 4.5) using dilute sulphuric acid. In addition to adding yet another pH adjustment step, the addition of sulphuric acid results in a slurry with a higher sulphur content, which can result waste disposal problems and raise environmental concerns. Another problem associated with using sulphuric acid for pH adjustment results in DDGS, an animal feed component with high sulphur content.

It is apparent that the need to adjust the pH of a slurry or mash to accommodate commercially-available enzyme preparations increases the numbers of steps required for grain processing and introduces ions and other chemicals into the slurry or mash that can adversely affect microorganism growth, the quality of the co-product, and the ease of disposing of process waste materials.

Another problem with conventional grain processing methods involves phytic acid (i.e., phytate, myo-inositol hexakis-phosphate, or IP6). Phytate is the primary storage form of phosphate in cereals/grains and oil seeds (see, e.g., Graf, E. (ed.) "Phytic acid Chemistry and Applications" (1986) Pilatus Press, Minneapolis, USA). Phytate consists of myo-inositol ring and six symmetrically distributed phosphate groups. Phytate is generally considered an undesirable component of grain and cereals for use in feed formulations because the phosphate is unavailable to monogastric animals due to its limited digestibility. Phytate is also known to bind essential minerals, such as zinc, iron, calcium, magnesium and proteins resulting in a reduction in their bioavailability (Maenz D. et al. (1997) *Anim. Feed. Sci.* 72:664-68; Ritter, M. et al. (1987) *J. Food Sci.* 52, 325-41). Phytate and other myo-inositol phosphate esters have also been shown to exhibit alpha-amylase inhibitory effects with respect to the hydrolysis of starch (Knuckles B. and Betschart, A. (1987) *J. Food Sci.* 52, 719-21).

Phytate hydrolyzing enzyme (i.e., phytase; myo-inositol hexaphosphate phosphohydrolase, E.C. 3.1.3.8) hydrolyses phytic acid into inorganic phosphates and inositol mono-to-penta-phosphates. The enzyme is widely distributed in plants, micro-organisms and animal tissues (Wodzinski, R. and Ullah, A. (1996) *Advances in Applied Microbiology* 42:264-303; Dvorakova J. (1998) *Folia Microbiol* 43:323-338). Plant phytases generally exhibit activity between pH 4.5 to 6.5, with a temperature optimum of 55° C. Thus, the processing conditions of animal feed formulation generally results in the complete inactivation of the endogenous phytases. As a consequence, microbial phytases are often used in feed formulations. Commercially available microbial phytases include Phyzyme™ XP 5000 from Genencor, Finase™ from AB Enzymes, GODO PHY™ from Godo Shusei Japan, Allzyme™ Phytase from Altech, Natuphos™ from BASF, Ronozyme™ P from DSM/Novozyme.

Pretreatment of cereals and grains with phytases to reduce phytic acid content has also been reported. For example, U.S. Pat. No. 4,914,029 describes a process for treating corn or sorghum kernels with phytase under steeping conditions in the presence of sulphur dioxide to eliminate or greatly reducing the phytin content in corn steep liquor. An enzymatic process using phytase for producing phytate free or low phytate soy protein isolate/concentrate is described in European Patent Pub. No. EP 380 343. U.S. Pat. No. 5,756,714 further describes enhanced hydrolysis of starch by an alpha-amylase under liquefaction conditions by pretreating the starch slurry with phytase. International Pat. Pub. No. WO 98/11788 describes a method for reducing the phytin content of the cereals product by subjecting to a combined wet steeping and dry steeping in at least two successive cycles whereupon activating the endogenous phytase for hydrolyzing the phytic acid. Finally, U.S. Pat. Pub. No. 2005/0272137 describes an improved fermentation process wherein phytic acid containing material is fermented in the presence of phytase.

The presence of phytic acid in grains impacts the ethanol production process by increasing the cost of waste disposal, reducing the amount of thin stillage that can be recycled, binding trace metals necessary for the growth of microorganisms, decreasing the activity of proteolytic enzymes, and reducing the rate and efficiency of starch hydrolysis by inhibiting alpha amylases.

It is therefore apparent that the need exists to reduce the amount of phytate present in grains and cereal-derived product.

BRIEF SUMMARY

Described are compositions and methods relating to the processing of grain/cereal starch into soluble dextrins and sugars. The compositions and methods feature a thermostable phytase, which avoids the need to adjust the pH of the grain/cereal slurry, obviates the need for low temperature phytase pretreatment, and allows liquefaction to proceed at unexpectedly high temperatures. In some embodiments, the compositions and methods allow the entire process of ethanol production, from starch liquefaction to fermentation, to be performed without a single pH adjustment.

In one aspect, a method for performing starch liquefaction in a slurry comprising starch and phytate is provided, the method comprising contacting the slurry with a thermostable phytase and an alpha-amylase under primary liquefaction or secondary liquefaction conditions, wherein the presence of the thermostable phytase increases the amount of starch liquefaction compared to an equivalent process in the absence of the phytase.

In some embodiments, the pH of the slurry is not adjusted before or after primary liquefaction, the secondary liquefaction, or both. In some embodiments, the alpha-amylase can be used at a pH lower than that at which it would be active in the absence of the phytase.

In some embodiments, the slurry does not require a phytase pretreatment step prior to primary liquefaction, for example, a pretreatment step at a temperature below about 70° C. In some embodiments, the phytase is added at a temperature that is not lower than about 80° C., 81° C., 82° C., 83° C., 84° C., or even 85° C.

In some embodiments, the temperature of primary liquefaction and secondary liquefaction is 75° C. or higher, for example, 80° C. or higher, 81° C. or higher, 82° C. or higher, 83° C. or higher, 85° C. or higher or even 90° C. or higher. In some embodiments, the temperature of primary liquefaction and secondary liquefaction is 85° C. or higher. In some embodiments, the temperature of secondary liquefaction is 90° C. or higher. In some embodiments, the slurry does not require the addition of an anti-oxidant.

In some embodiments, the phytase is obtained from a *Buttiauxella* spp. In some embodiments, the phytase is a recombinant thermostable phytase derived from a *Buttiauxella* spp. phytase. In some embodiments, the phytase is selected from BP-110 (SEQ ID NO: 3), BP-111 (SEQ ID NO: 4), and BP-112 (SEQ ID NO: 5). In particular embodiments, the phytase is BP-111 (SEQ ID NO: 4).

In some embodiments, the alpha-amylase is a thermostable alpha-amylase. In particular embodiments, the alpha-amylase is derived from *Bacillus licheniformis* or *Geobacillus stearothermophilus*, or it a combination of alpha-amylases from these organisms.

In another aspect, method for performing starch liquefaction in a slurry that includes granular starch and phytate is provided, the method comprising:

(a) preparing a slurry comprising granular starch and thin stillage, (b) contacting the slurry with a thermostable phytase and a thermostable alpha-amylase, (c) performing primary liquefaction and secondary liquefaction, and (d) using dextrins produced in step (c) for fermentation, wherein the pH of the slurry is not adjusted in any of steps (a)-(d).

In some embodiments, the slurry does not require a phytase pretreatment step prior to primary liquefaction. In some embodiments, thermostable phytase and thermostable alpha-amylase are added together or separately at a temperature of 75° C. or higher, for example, 80° C. or higher, 81° C. or higher, 82° C. or higher, 83° C. or higher or even 85° C. or higher. In some embodiments, the slurry does not require the addition of an anti-oxidant.

In some embodiments, the phytase is a recombinant thermostable phytase derived from a *Buttiauxella* spp. phytase. In some embodiments, the phytase is selected from BP-110 (SEQ ID NO: 3), BP-111 (SEQ ID NO: 4), and BP-112 (SEQ ID NO: 5). In particular embodiments, the phytase is BP-111 (SEQ ID NO: 4).

In some embodiments, the alpha-amylase is derived from *Bacillus licheniformis* or *Geobacillus stearothermophilus*, or it a combination of alpha-amylases from these organisms.

These and other aspects and embodiments of the compositions and methods will be apparent from the present description and drawings.

BRIEF DESCRIPTION OF THE DRAWINGS

FIG. 4 shows and alignment of the exemplary *Buttiauxella* sp. thermostable phytases BP-17 (SEQ ID NO: 2), BP-110 (SEQ ID NO: 3), BP-111 (SEQ ID NO: 4), and BP-112 (SEQ ID NO: 5), with the wild-type *Buttiauxella* sp. phytase (SEQ ID NO: 1).

DETAILED DESCRIPTION

I. Definitions

Figure 1:
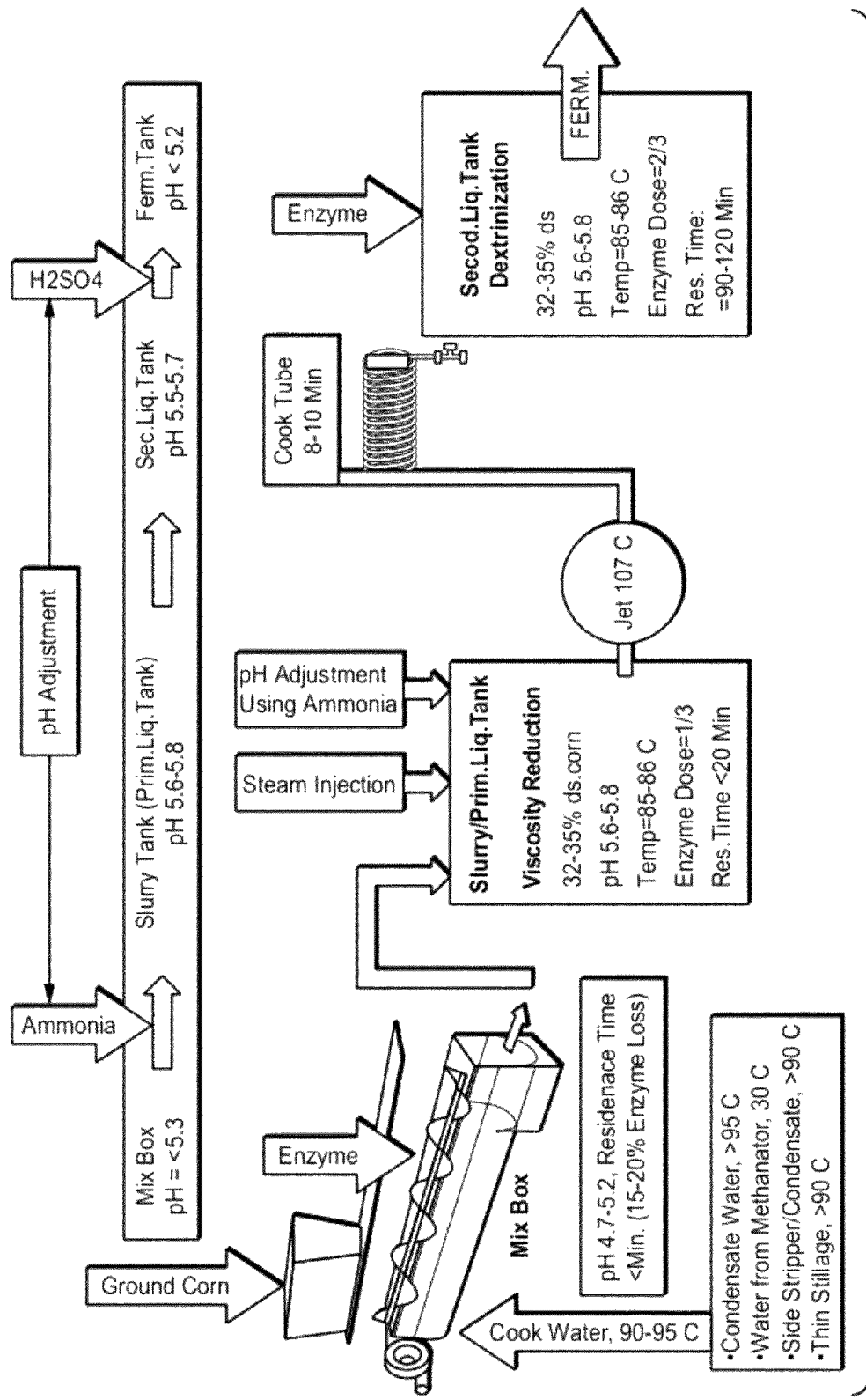
FIG. 1 is a diagram illustrating the steps in a conventional liquefaction process for producing ethanol using whole ground grain with pH adjustment.
Figure 2:
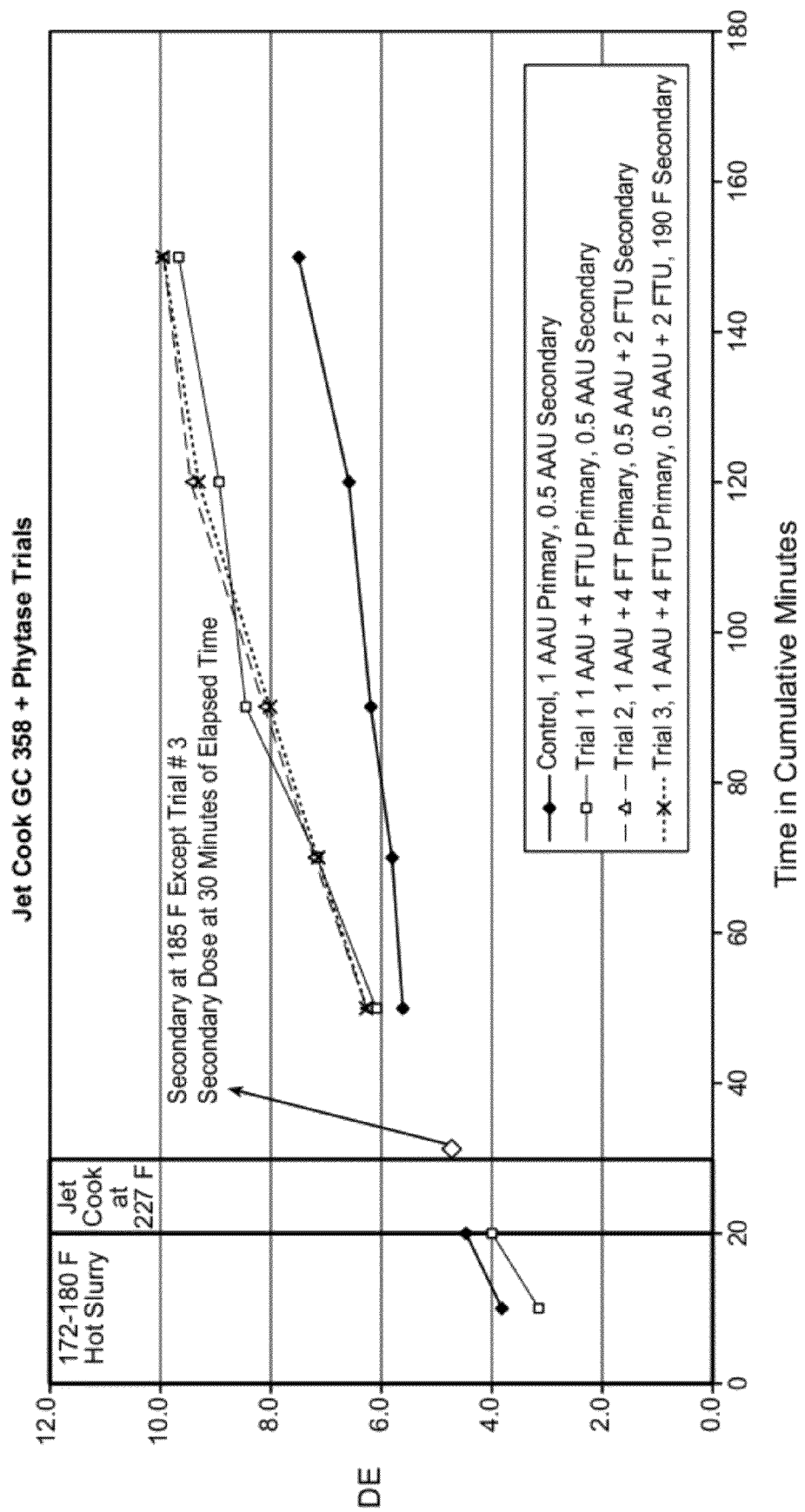
FIG. 2 is a graph showing that the addition of phytase to whole ground corn results in the increased low-pH stability and high-temperature stability of an exemplary alpha amylase.

Prior to describing the present compositions and methods, the following terms are defined for clarity. Other definitions may appear throughout the document. Common abbreviations are listed at the beginning of the "Examples" section.

As used, herein, the terms "liquefaction" or "liquefy" refer to a process by which starch is converted to shorter chain and less viscous dextrins. The process may involve more than one step.

As used, herein, the term "dextrins" refers to short chain polymers of glucose (e.g., 2 to 10 units).

As used herein, the term "starch" refers generally to a complex polysaccharide carbohydrates of plants consisting of a large number of glucose units joined together by glycosidic bonds and having the formula $(C_6H_{10}O_5)_x$, wherein x can be any number. Starch includes amylose and amylopectin.

As used, herein, the term "granular starch" refers to raw starch that has not been subjected to temperatures of gelatinization. and "glucoamylase" (E.C. 3.2.1.3) are used interchangeably to As used, herein, the terms "saccharifying enzyme" refers to an enzyme that is capable of catalyzing the release of D-glucose from the non-reducing ends of starch and related oligo and polysaccharides. Saccharifying enzymes include glucoamylases (E.C. 3.2.1.3).

As used, herein, the term "oligosaccharides" refers to a compound having 2 to 10 monosaccharide units joined in glycosidic linkages. These short chain polymers of simple sugars include dextrins.

As used herein, the term "dextrose equivalent" (or "DE") refers to an industry standard for measuring the concentration of total reducing sugars, calculated as the amount of D-glucose present (or produced) on a dry weight basis. Unhydrolyzed granular starch has a DE that is essentially 0 and D-glucose has a DE of 100.

As used herein, the term "glucose syrup" refers to an aqueous composition containing glucose solids. Glucose syrup has a DE of at least 20. Glucose syrup may contain no more than 21% water and no less than 25% reducing sugar, calculated as dextrose. Glucose syrup may include at least 90% D-glucose or even at least 95% D-glucose. The terms glucose and glucose syrup are used interchangeably unless otherwise apparent from context.

As used herein, the term "total sugar content" refers to the total sugar content present in a starch composition.

As used herein, the term "dry solids" (or "DS") refers to the total solid material present in a slurry expressed as % on a dry weight (wt/wt) basis.

As used herein, the term "fermentation" refers to the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

As used herein, the phrase "simultaneous saccharification and fermentation" (or "SSF") refers to a process in the production of end products in which a fermenting organism, such as an ethanol producing microorganism, and at least one enzyme, such as a saccharifying enzyme, are combined in the same process step in the same vessel.

As used herein, the term "end product" refers to a carbon-source-derived product that is enzymatically converted from a fermentable substrate. The end product may be an alcohol, such as ethanol.

As used herein, the term "derived" encompasses the terms "originated from," "obtained from," "obtainable from," and "isolated from," as intended to describe a relationship between specified objects.

As used herein, the term "fermenting organism" refers to a microorganism or cell that is suitable for use in fermentation to directly or indirectly produce an end product.

As used herein, the term "ethanol producer" or "ethanol producing microorganism" refers to a fermenting organism that is capable of producing ethanol from a mono- or oligosaccharide.

As used herein, the terms "recovered," "isolated," and "separated," with reference to a protein, cell, nucleic acid or amino acid, indicate that the protein, cell, nucleic acid or amino acid, is removed from at least one component with which it is naturally associated.

As used herein, the term "contacting" means to bring into juxtaposition as through mixing. Contacting may occur by in solution by mixing two liquid reagents or one liquid reagent and a solid material.

As used herein, the terms "protein" and "polypeptide" are used interchangeability to refer to a chain of amino acid residues linked by peptide bonds. Unless otherwise specified, amino acid sequences are written in an N-terminal to C-terminal direction using the conventional one-letter and three-letter codes for amino acid residues. It will be appreciated that due to the degeneracy of the genetic code the same polypeptide may be encoded by more than one nucleotide sequence.

As used herein, the term "thin stillage" refers to the liquid portion of stillage separated from solids by screening or centrifuging. Thin stillage contains suspended fine particles and dissolved material. It is normally sent to evaporator to be concentrated to thick syrup and then dried with the solids portion to produce distillers grain with solubles (DDGS).

As used herein, the term "backset" refers to recycled thin stillage. Backset may be added to a slurry or to a fermentor to serve as a source of yeast nutrients and/or to reduces the amount of water required for mashing.

As used herein, the term "condensate" refers to liquid condensed from vapor, e.g., in a condenser or a heat exchanger device, which may be connected to a vapor discharge pipe of a column to permit the vapor to be cooled and condensed to be a liquid.

As used herein, the term "cook water" refers to water used in the ethanol industry as make up water for producing grain slurry. It is generally a mixture of thin stillage, condensate water, and fresh water.

As used herein, the term "primary liquefaction" refers to the incubation of a whole ground-grain slurry containing thin stillage solids with enzymes (e.g., alpha-amylase and phytase) before jet cooking. Primary liquefaction is typically performed at 80-90° C.

As used herein, the term "secondary liquefaction" refers to the hydrolysis of gelatinized starch with a second dose of enzymes after jet cooking.

As used herein, the term "hydrolyzing phytic acid" refers to hydrolyzing inositol hexaphosphate phosphohydrolase (IP6) to a molecule that contains less than six phosphates, e.g., IP5, IP4, IP3, and the like. Preferably, at least 50% of the phytate present is hydrolyzed.

The singular forms "a," "an," and "the" include plural referents unless the context clearly dictates otherwise. Where a range of values is provided, it is understood that each intervening value, to the tenth of the unit of the lower limit, is also specifically disclosed, unless otherwise apparent from context. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included. All references cited herein are expressly incorporated by reference.

II. Overview of the Composition and Methods

The present compositions and methods relate to the use of a thermostable phytase in a starch liquefaction process. Without being limited to a theory, it is believed that phytate (i.e., IP6) acts as both a non-competitive inhibitor of alpha-amylase (e.g., by interacting with amino and other positively-charged residues on the surface of the enzyme and chelating calcium) and a competitive inhibitor (e.g., by interacting with the active site). The presence of phytate in a slurry or mash reduces the stability of alpha-amylases, which is reflected by reduced activity, reduced thermostability, and reduced low pH stability. The additional of phytase to a slurry or mash successively hydrolyzes phytate to IP5, IP4, IP3, IP2, and the like, which are less detrimental to the stability of the alpha-amylase. Increasing the stability of the alpha-amylase allows liquefaction to proceed under lower pH condition and at higher temperatures.

While the addition of a phytase during liquefaction or fermentation has been described, this process required performing a phytase pretreatment step at a temperature of less than about 70° C. to avoid inactivation of the phytase (see, e.g., WO 2008/097619). It has heretofore not been possible to add phytase to whole ground grain under the liquefaction conditions without any process modifications (e.g., a lower temperature pretreatment step) to avoid inactivating the phytase. The use of a thermostable phytase under primary and/or secondary liquefaction conditions eliminates the need for phytase pretreatment below 70° C. and allows the entire liquefaction process to be performed at a temperature of at 80° C. or greater.

The efficient removal of phytic acid that is achieved using a thermostable phytase allows primary and secondary liquefaction to be performed without the need to adjust the pH of the slurry or mash above, e.g., about pH 5.6. Such pH adjustment is a key step in conventional starch liquefaction. pH adjustment not only introduces additional steps to the liquefaction process, it add salts and/or other chemical that can interfere with subsequent organism growth, the properties of end products, and/or the cost of waste disposal. Thus, the ability to perform liquefaction without adjusting the pH of the slurry, and without a lower temperature phytase pretreatment step prior to high temperature cooking, offers the solution to an unmet need in the ethanol industry, resulting in numerous processing advantages.

The use of a thermostable phytase also appears to extend the temperature range at which thermostable amylases are able to function. For example, it is generally accepted that secondary liquefaction temperatures above 85° C. (185° F.) result in reduced dextrinization due to inactivation of alpha-amylases. However, data generated in support of the present compositions and methods show that the use of a thermostable phytase in primary liquefaction (performed at 85° C. (185° F.)), without any pH adjustment, allows the secondary liquefaction step to be performed at about 87.7° C. (190° F.) with no performance penalty.

Yet another benefit of liquefaction of whole ground corn at lower pH and high temperature may be to reduce the loss of fermentable sugars due to the Mailard reaction between amino acids and reducing sugars. The Mailard reaction is accelerated in an alkaline environment, which is avoided by maintaining the slurry at a lower pH.

These and other features and advantages of the present compositions and methods will be apparent from the following description.

III. Enzymes Suitable for Use in the Composition and Methods

Various phytases and alpha-amylases are suitable for use in the present compositions and methods. Exemplary enzymes are described, below.

A. Phytases

Phytases suitable for use in the present compositions and methods may be from any microbial source, including but not limited to a fungal or bacterial source. The phytase should be capable of hydrolyzing phytic acid under the conditions of primary and secondary liquefactions. Preferred phytases are capable of hydrolyzing at least 50% of phytate present in a slurry or mash under the conditions of primary and secondary liquefactions. Preferred phytases are thermostable, meaning that they are capable of hydrolyzing at least 50% of phytate present in a starch-containing grain slurry or mash (e.g., comprising about 32% DS) in about 20 minutes at a temperature of at least 80° C., and even at a temperature of at least 81° C., at least 82° C., at least 83° C., at least 84° C., or at least 85° C.

Exemplary thermostable phytases can be obtained from *Buttiauxella* spp, such as *B. agrestis, B. brennerae, B. ferragutiase, B. gaviniae, B. izardii, B. noackiae*, and *B. warmboldiae*. Strains of *Buttiauxella* spp. are available from DSMZ, the German National Resource Center for Biological Material. An exemplary strain is *Buttiauxella* sp. strain P1-29 deposited under accession number NCIMB 41248. Phytases may be identified from *Buttiauxella* spp. by methods described in WO 06/043178, including but not limited to hybridization techniques. Phytases may be recombinant polypeptides, including engineered variant polypeptides.

Examples of recombinant thermostable variant *Buttiauxella* spp. phytases are BP-110 (SEQ ID NO: 3), BP-111 (SEQ ID NO: 4), and BP-112 (SEQ ID NO: 5). The thermostability of these phytases is described in detail in Examples 5-11. The substitutions in these variants that give rise to their advantageous thermostable properties compared to the wild-type phytase (SEQ ID NO: 1) and BP-17 (a moderately thermostable variant; SEQ ID NO: 2; see, e.g., WO 2008/097619) are apparent from the alignment of amino acid sequences shown in FIG. 4 and from the Examples. Other variants that include different combinations of the substitutions in BP-110, BP-111, or BP-112, or other mutation in addition to one or more of these substitutions, are expected to have similar properties.

B. Alpha-Amylases

Alpha-amylases suitable for use in the present compositions and methods may be from any source, including a microbial source, such as from fungi or bacteria, or a plant source. In some embodiments, the alpha-amylase is an acid stable alpha-amylase, which is active in the pH range of 3.0 to 7.0, and preferably in the pH range of 3.5 to 6.5.

Exemplary alpha-amylases can be obtained from bacterial strains including *Bacillus* spp., such as *B. licheniformis*, *Geobacillus* (formerly *Bacillus*). *stearothermophilus*, *B. amyloliquefaciens*, *B. subtilis*, *B. lentus*, and *B. coagulans*. Alpha-amylases from *B. licheniformis*, *G. stearothermophilus*, and *B. amyloliquefaciens* are particularly well characterized. Suitable bacterial alpha-amylases are described in, e.g., U.S. Pat. Nos. 5,093,257, 5,763,385, 5,824,532, 5,958,739, 6,008,026, 6,093,563, 6,187,576, 6,361,809, 6,939,703, 6,080,568, 5,736,499, 4,717,662, 6,218,164, 6,008,026, 6,211,134, 6,432,689, 6,100,073, and 5,364,782; U.S. Pat. Pub. No. 2006/0014265, 2005/0112237, and 2007/0141693; International Pat. Pub. Nos. WO 96/23874, WO 96/39528, WO 97/141213, WO 99/19467, WO 05/001064, WO 94/183314, WO 95/35382, WO 99/09183, WO 98/26078, WO 99/02702, WO 97/43424, WO 99/29876, WO 97/10342, WO 96/02633, WO 91/00353, WO 05/111203, WO 05/007867, WO 07/007,053, WO 06/089107, and WO 08/021,050; and European Pat. Pubs. EP 0 942 994 and EP 1 848 735.

Commercially available alpha-amylases suitable for use in the compositions and method include SPEZYME™ AA, SPEZYME™ FRED, SPEZYME™ XTRA, GZYME™ 997, and GC 358, and blends of alpha-amylases from *Bacillus licheniformis* and *Bacillus stearothermophilus* including CLEARFLOW® and TERMAMYL™ 120-L, LC, SC, and SUPRA (all from Genencor International, Inc.). Additional alpha-amylases are LIQUOZYME™ X (Novozymes A/S) and Fuelzyme™ LF (Verenium LLC).

The exemplary alpha-amylases used in experiments performed in support of the compositions and methods were SPEZYME™ FRED, which includes a variant *B. licheniformis* alpha-amylase having the substitutions M15T, H133Y, N188S, and A209V (see, e.g., U.S. patent application Ser. No. 12/263,886, filed 3 Nov. 2008); GC 358, which includes a variant *G. stearothermophilus* alpha-amylase having the substitution S242Q (see, e.g., U.S. Pat. No. 5,958,739); and SPEZYME™ XTRA, which includes a truncated *G. stearothermophilus* alpha-amylase. Note that any of the above-described alpha-amylases can be used in combination.

C. Glucoamylases

The present compositions and methods may optionally include a glucoamylase (GA; E.C. 3.2.1.3.) for use as a saccharifying enzyme. The glucoamylase may be derived from the heterologous or endogenous protein expression of bacteria, plants and fungi sources. Preferred glucoamylases are produced by strains of filamentous fungi and yeast. Glucoamylases secreted from strains of *Aspergillus* and *Trichoderma* are commercially available. Suitable glucoamylases include naturally occurring wild-type glucoamylases as well as variant and genetically engineered mutant glucoamylases. Examples of suitable glucoamylases are *Aspergillus niger* G1 and G2 glucoamylases (Boel et al. (1984) *EMBO J.* 3:1097-1102; WO 92/00381, WO 00/04136; and U.S. Pat. No. 6,352,851); *Aspergillus awamori* glucoamylases (WO 84/02921); *Aspergillus oryzae* glucoamylases (Hata et al. (1991) *Agric. Biol. Chem.* 55:941-49); and *Aspergillus shirousami* glucoamylases (e.g., Chen et al. (1996) *Prot. Eng.* 9:499-505; Chen et al. (1995) *Prot. Eng.* 8:575-82; and Chen et al. (1994) *Biochem J.* 302:275-81). Glucoamylases can also be obtained from strains of *Talaromyces*, such as those derived from *T. emersonii*, *T. leycettanus*, *T. duponti* and *T. thermophilus* (WO 99/28488; U.S. Pat. Nos. RE: 32,153 and 4,587,215), strains of *Trichoderma*, such as *T. reesei*, and particularly glucoamylases having at least 80%, 85%, 90% and 95% sequence identity to SEQ ID NO: 4 disclosed in U.S. Pat. Pub. No. 2006/0094080, strains of *Rhizopus*, such as *R. niveus* and *R. oryzae*; strains of *Mucor*, and strains of *Humicola*, such as *H. grisea* (e.g., Boel et al. (1984) *EMBO J.* 3:1097-102; WO 92/00381; WO 00/04136; Chen et al. (1996) *Prot. Eng.* 9:499-505; Taylor et al. (1978) *Carbohydrate Res.* 61:301-08; U.S. Pat. No. 4,514,496; U.S. Pat. No. 4,092,434; and Jensen et al. (1988) *Can. J. Microbiol.* 34:218-223). Other glucoamylases include those obtained from *Athelia rolfsii* and variants thereof (WO 04/111218).

Commercially available glucoamylases are produced, e.g., from *Aspergillus niger* (e.g., DISTILLASE™, OPTIDEX™ L-400, G ZYME™ G990 4X, and OPTIMAX™4060 VHP, all from Genencor) and *Rhizopus* spp. (e.g., CU.CONC™ from Shin Nihon Chemicals, Japan). Another commercially available enzyme is GLUCZYME™ (Amano Pharmaceuticals, Japan; Takahashi et al. (1985) *J. Biochem.* 98:663-71). Additional enzymes include three forms of glucoamylase of a *Rhizopus* sp., namely "Gluc1" (MW 74,000), "Gluc2" (MW 58,600), and "Gluc3" (MW 61,400), and G Zyme 480 Ethanol (Genencor).

D. Compositions and Formulations

Enzyme compositions for use as described include blended or formulated enzyme compositions. In some embodiments, one or more phytases and one or more alpha amylase are provided together in a blend, which may be added to a slurry or mash. In such cases, the blend represents a single phytase/amylase composition for use in a starch conversion process that does not require a pH adjustment. In other embodiments, one or more phytases and one or more alpha amylase are provided separately in different compositions or formulations. In such cases, the phytase and amylase compositions may represents a single phytase/amylase kit for use in a starch conversion process that does not require a pH adjustment. A glucoamylase may optionally be added to the phytase/amylase blend, to either the phytase or amylase composition, or provided separately for addition to a slurry or mash.

The phytase composition and alpha amylase composition may be present in a blend, or separately added to a slurry or mash in a ratio of phytase (FTU/g DS) to alpha amylase (AAU/g DS) of 15:1 to 1:15, including 10:1 to 1:10, 5:1 to 1:5 and 3:1 to 1:2.

IV. Starch-Containing Materials

Granular starch for processing may be obtained from plant material including but not limited to wheat, corn, rye, sorghum (milo), rice, millet, barley, triticale, cassava (tapioca), potato, sweet potato, sugar beets, sugarcane, and legumes such as soybean and peas. Preferred plant material includes corn, barley, wheat, rice, milo and combinations thereof. Plant materials include hybrid varieties and genetically modified varieties (e.g., transgenic corn, barley or soybeans comprising heterologous genes). Any part of the plant may be used to provide granular starch including but not limited to plant parts such as leaves, stems, hulls, husks, tubers, cobs, grains and the like. In some cases, essentially the entire plant may be used, for example, the entire corn stover may be used. In some cases, whole grain may be used as a source of granular starch. Preferred whole grains include corn, wheat, rye, barley, sorghum and combinations thereof. In other cases, granular starch may be obtained from fractionated cereal grains including fiber, endosperm and/or germ components. Plant material may be obtained from different sources (e.g. corn and Milo or corn and barley) and mixed together to obtain granular starch.

Methods for fractionating plant material such as corn and wheat are known in the art. Plant material comprising granular starch may be prepared by means such as milling. Two general milling processes are wet milling and dry milling. In dry milling, the whole grain is milled and used in the process. In wet milling, the grain is separated (e.g., the germ from the meal). Means of milling whole cereal grains are well known and include the use of hammer mills and roller mills.

V. Methods of Use

The present methods relate to the use of a thermostable phytase to increase the amount or rate of starch liquefaction in a starch liquefaction process involving an alpha-amylase. Moreover, the present methods obviate the need for a low temperature (i.e., less than about 70° C.) phytase pretreatments step, obviate the need for pH adjustment before, during, and/or after the liquefaction process, increase the temperature range of alpha-amylases, and/or obviate the need to add anti-oxidants to protect the alpha-amylase from degradation.

In one embodiment, a method for producing ethanol by fermentation is provided, involving producing whole ground grain slurry (20-50% w/w) using 10-70% v/v thin stillage, condensate water, and/or fresh water (also called cook water), and adding to the slurry, without any pH adjustment, a thermostable phytase and a thermostable alpha amylase, wherein the phytase removes phytic acid to enhance the low pH thermostability of the thermostable alpha amylase. The thermostable alpha amylase may also be added together with phytase or after the phytase, e.g., to allow the phytase to remove hydrolyze phytate prior to the addition of the amylase. The treated slurry may then be cooked at a high temperature with or without jet cooking in presence of the thermostable alpha amylase. Where jet cooking is used, the temperature is typically raised up to about 45° C. above the starch gelatinization temperature. (e.g. to 65° C. to 120° C., 70° C. to 110° C., or 70° C. to 90° C.) for a period of time of about 2 min to 6 hr (e.g., 2 min to 4 hr or 1 hr to 2 hr). An addition amount of the thermostable alpha-amylase may optionally be added to the slurry and liquefaction allowed to continue, again, without the requirement for pH adjustment.

The slurry may include 15-55% DS (e.g., 20-50%, 25-45%, 25-40%, and 20-35% DS). The slurry may also include 10-70% v/v thin stillage (e.g., 10-60%, 10-50%, 20-50%, 10-40%, 20-40%, or 10-30%). Granular starch in the slurry may be contacted with phytase for a period of 5 min to 8 hr (e.g., 5 min to 6 hr, 5 min to 4 hr, or 30 min to 4 hr) along with alpha-amylase or prior to the addition of amylase. The temperature at which the phytase is added may be above 80° C., above 81° C., above 82° C., above 83° C., above 84° C., and even above 85° C.

The slurry may have a pH of about 4.8 to less than about 5.5, e.g., about 5.2 to 5.5, and need not be adjusted prior to the addition of alpha-amylase. Accordingly, phytase treatment and liquefaction may both be performed at the "natural" pH of slurry. The addition of a thermostable phytase may also allow the process of starch liquefaction to be performed at a pH lower than if the alpha amylase was used without the phytase. For example, the starch liquefaction process may be conducted at a pH of about 0.5 to 1.5 units lower (e.g., 0.2, 0.3, 0.4, 0.5, 0.7, 0.8, 1.0, 1.2 or 1.5 pH units lower) than if the alpha-amylase was used without the phytase.

The amount (dosage) of phytase used in the liquefaction process may be in the range of about 0.001 to 50 FTU/g DS, preferably 0.01 to 10 FTU/g DS, and even 0.05 to 5.0 FTU/g DS or 0.5 to 5.0 FTU/g DS. Exemplary amounts are 0.5 FTU/g DS, 1 FTU/g DS, 2 FTU/g DS, 3 FTU/g DS, 4 FTU/g DS, and 5 FTU/g DS. The amount of alpha-amylase will be an effective amount as known to a person of skill in the art, e.g., 0.1 to 50 AAU/g DS, and preferably 1 to 10 AAU/g DS.

The method may further comprise using the liquefied starch, without any further pH adjustment, as a fermentation feedstock for ethanol fermentation. Accordingly, the entire process of grain processing, from starch conversion to ethanol production, can be performed without a single pH adjustment. Fermentation methods are known in the art and generally include the addition of saccharifying enzymes such as glucoamylases, and optionally other secondary enzymes. The saccharification process may last for about 12-120 hr; however, it is common to perform a pre-saccharification step for 30 min to 2 hr and then to complete saccharification during fermentation. Sometimes this is referred to as simultaneous saccharification and fermentation (SSF). Saccharification is commonly carried out at temperatures of about 30-65° C. and typically at pH of about 4.0 to 5.0.

The organism used in fermentation depend on the desired end product. If ethanol is the desired end product yeast are typically used as the fermenting organism. An exemplary ethanol-producing microorganism is a *Saccharomyces* spp., such as *S. cerevisiae* (see, e.g., U.S. Pat. No. 4,316,956). A variety of *S. cerevisiae* are commercially available and include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast used should be effective to produce a commercially significant amount of ethanol in a suitable amount of time (e.g., to produce at least 10% ethanol from a substrate having between 25-40% DS in less than 72 hr). Yeast cells are generally supplied in amounts of $10^4$ to $10^{12}$, and preferably from $10^7$ to $10^{10}$ viable yeast count per ml of fermentation broth. The fermentation process may include, in addition to a fermenting microorganisms, nutrients, optional acids, and additional enzymes, including but not limited to phytases and glucoamylases.

The use of yeast in fermentation is well known and reference is made to THE ALCOHOL TEXTBOOK, K. JACQUES ET AL., EDS. 1999, NOTTINGHAM UNIVERSITY PRESS, UK. In some embodiments, the amount of ethanol produced by the methods encompassed by the invention will be at least 8%, at least 10%, at least 12%, at least 14%, at least 15%, at least 16%, at least 17% and at least 18% (v/v). and at least 23% v/v. Optionally following fermentation, alcohol (e.g., ethanol) may be extracted by, e.g., distillation. Ethanol may be used for fuel, portable or industrial ethanol.

End-products such as alcohol (e.g., ethanol), organic acids (e.g., succinic acid, lactic acid), sugar alcohols (e.g., sorbitol), ascorbic acid intermediates (e.g., gluconate, DKG, KLG), amino acids (e.g., lysine), proteins (e.g., antibodies and fragment thereof), biochemicals, and enzymes may be produced using suitable organisms, optionally followed by chemical modification or synthesis steps.

Other related compositions and methods will be apparent from the foregoing description and following Examples. All reference cited herein are incorporated by reference in their entirety.

EXAMPLES

The following general methods and examples are offered to illustrate, but not to limit the present composition and methods. In the disclosure and experimental sections that follow, the following abbreviations apply: wt % (weight percent); ° C. (degrees Centigrade); $H_2O$ (water); $dH_2O$ (deionized water); $dIH_2O$ (deionized water, Milli-Q filtration); g or gm (grams); μg (micrograms); mg (milligrams); kg (kilograms); μL (microliters); ml and mL (milliliters); mm (millimeters); μm (micrometer); M (molar); mM (millimolar); μM (micromolar); U (units); MW (molecular weight); sec (seconds); min(s) (minute/minutes); hr(s) (hour/hours); ° C. (degrees Centigrade); DS (dry solids); DO (dissolved oxygen); W/V (weight to volume); WAN (weight to weight); V/V (volume to volume); Genencor (Genencor International, Inc., Palo Alto, Calif.); IKA (IKA Works Inc. 2635 North Chase Parkway SE, Wilmington, N.C.); MT (Metric ton); DE (dextrose equivalents); EtOH (ethanol); HPLC (high pressure liquid chromatography); SSU (soluble starch unit); DP (degree of polymerization); GAU (glucoamylase activity units); distillers dried grains with solubles (DDGS); AAU (alpha amylase activity unit); and PNPG (p-nitrophenyl-alpha-D-glucopyranoside). Some of these abbreviations are also used above.

General Methods

1. Carbohydrate Analysis by HPLC

The compositions of oligosaccharide reaction products were measured using an HPLC (Beckman System Gold 32 Karat Fullerton, Calif., USA) equipped with an appropriate column (Rezex 8 u8% H, Monosaccharides) maintained at 50° C. The instrument was fitted with a refractive index (RI) detector (ERC-7515A, RI Detector (Anspec Company Inc.). Saccharides were separated based on molecular weight and compared with standards. The designation "DP1" refers to a monosaccharide, such as glucose; the designation "DP2" refers to a disaccharide, such as maltose; the designation "DP3" refers to a trisaccharide, such as maltotriose; and the designation "DP4$^+$" refers to an oligosaccharide having a degree of polymerization (DP) of 4 or greater.

2. Phytase Activity Measurement

Phytase activity units (FTU) were measured by the release of inorganic phosphate. Inorganic phosphate forms a yellow complex with acidic molybdate/vandate reagent, which yellow complex can be measured at a wavelength of 415 nm in a spectrophotometer. The amount of released inorganic phosphate was quantified with the aid of a phosphate standard curve. One unit of phytase (FTU) is the amount of enzyme required to releases 1 μmole of inorganic phosphate from phytate per minute under the reaction conditions given in the European Standard (CEN/TC 327,2005-TC327WI 003270XX)

3. Phytic Acid Content Measurement

Phytic acid content was measured by extracting phytic acid from a sample by adjusting the pH of the 5% slurry (if it was dry sample) to pH 10, and then applying it to an HPLC ion exchange column. Phytic acid was eluted from the column using a NaOH gradient and the amount calculated with the aid of a phytic acid standard curve.

4. Alpha Amylase Activity Measurement

Alpha amylase activity units (AAU) were determined by the rate of starch hydrolysis, as reflected in the rate of decrease of iodine-staining capacity measured spectrophotometrically. One AAU of bacterial alpha-amylase activity is the amount of enzyme required to hydrolyze 10 mg of starch per min under standardized conditions. Alpha-amylase activity can also be measured as soluble starch units (SSU) based on the degree of hydrolysis of soluble potato starch substrate (4% DS) by an aliquot of the enzyme sample at pH 4.5, 50° C. The reducing sugar content is measured using the DNS method as described in Miller, G. L. (1959) *Anal. Chem.* 31:426-28.

5. Glucoamylase Activity Measurement

Glucoamylase Activity Units (GAU) were determined using a PNPG assay, which measures the ability of glucoamylase enzyme to catalyze the hydrolysis of PNPG to glucose and p-nitrophenol. At an alkaline pH the nitrophenol forms a yellow color that can be measured spectrophotometrically at 400 nm and used in the calculation of GAU. One GAU is the amount of enzyme required to liberate one gram of reducing sugars calculated as glucose from a soluble starch substrate per hour under the specified conditions of the assay.

Example 1

Increase in Variant *G. stearothermophilus* Alpha-Amylase Performance Using a Thermostable Phytase A first series of experiments was performed to determine if the presence of a thermostable phytase could increase the performance of a commercially-available alpha-amylase without adjusting the pH of the slurry as required using conventional compositions and methods. The experiments were carried out using 32% ds ground corn, with thin stillage making up 35% of the liquid phase. 81.9 kilograms of liquid adjusted to pH 4.8 was heated to 196° F. and 24 kilograms of ground corn was added. Note that in this experiment the pH of the slurry was lowered to pH 4.8 to simulate the low pH conditions of the cook water, not raised as would be necessary to stabilize an alpha-amylase in a conventional process.

The enzyme(s) were added and the remaining 24 kilograms of corn was added. After 20 minutes of hydrolysis at 180-182° F., the hot slurry was pumped at 6.3 liters/min through a steam injection cooker, known in the industry as Hydrothermal brand model M 103, set at 227° F. This temperature was maintained for 4.5-5 minutes by holding in delay loops equipped with a back pressure valve maintained at ~20 psi. The material exiting the system was allowed to flash to atmospheric pressure and samples were collected for performing secondary liquefaction at 185° F.

The dose and sampling scheme is shown in Table 1. The exemplary alpha-amylase was GC 358 (a variant of *G. stearothermophilus* alpha-amylase including the substitution S242Q). The dose is given in AAU/g DS corn. The exemplary thermostable phytase was BP 111 (SEQ ID NO: 3). The dose is given in FTU/g DS corn. Dextrose equivalents (DE) measured at various intervals following secondary liquefaction are shown in Table 2.

TABLE 1

Dosing and sampling.

| test | Hot Slurry Temp | Jet Temp | Primary Dose GC 358 | BP 111 | Seconday Dose GC 358 | BP 111 | Secondary Temp. |
|---|---|---|---|---|---|---|---|
| Control | 180-182 | 227 | 1 | 0 | 0.5 | 0 | 185 |
| Trial 1 | 180-182 | 227 | 1 | 4 | 0.5 | 0 | 185 |
| Trial 2 | 180-182 | 227 | 1 | 4 | 0.5 | 2 | 185 |
| Trial 3 | 180-182 | 227 | 1 | 4 | 0.5 | 2 | 190 |

TABLE 2

DE Progression with time at secondary liquefaction (pH 5.2, 185° F. and 190° F.) with and without phytase addition at primary liquefaction.

| | Hot Slurry | | Secondary Liquefaction Minutes | | | | | % phytic acid removed |
|---|---|---|---|---|---|---|---|---|
| | 10 | 20 | 50 | 70 | 90 | 120 | 150 | 0 |
| Control | 3.8 | 4.4 | 5.6 | 5.8 | 6.2 | 6.6 | 7.5 | |
| Trial 1 | 3.1 | 4.0 | 6.1 | 7.1 | 8.4 | 8.9 | 9.6 | 95 |
| Trial 2 | — | — | 6.3 | 7.2 | 8.1 | 9.5 | 9.9 | 95 |
| Trial 3 | — | — | 6.3 | 7.1 | 8.0 | 9.3 | 10.0 | 95 |

The DE development shown in Table 2 is evidence of alpha amylase activity, and is herein referred to as apparent alpha amylase activity. The 20-minute treatment with thermostable phytase clearly resulted in an increase in apparent alpha amylase activity, presumably due to the removal of phytic acid. Note that a non-thermostable phytase would have been inactivated at these slurry temperatures (see, e.g., Examples 9-11). Linear regression performed on the data shown in Table 2 demonstrated that the slope of the control line (i.e., slurry with no phytase), from 50 to 150 minutes, was 0.019 DE/min, while the slope of the test line (i.e., slurry with phytase), over the same period, was 0.038 DE/min. Thus, the addition of the phytase approximately doubled the effectiveness of the same amount of alpha-amylase.

Figure 3:
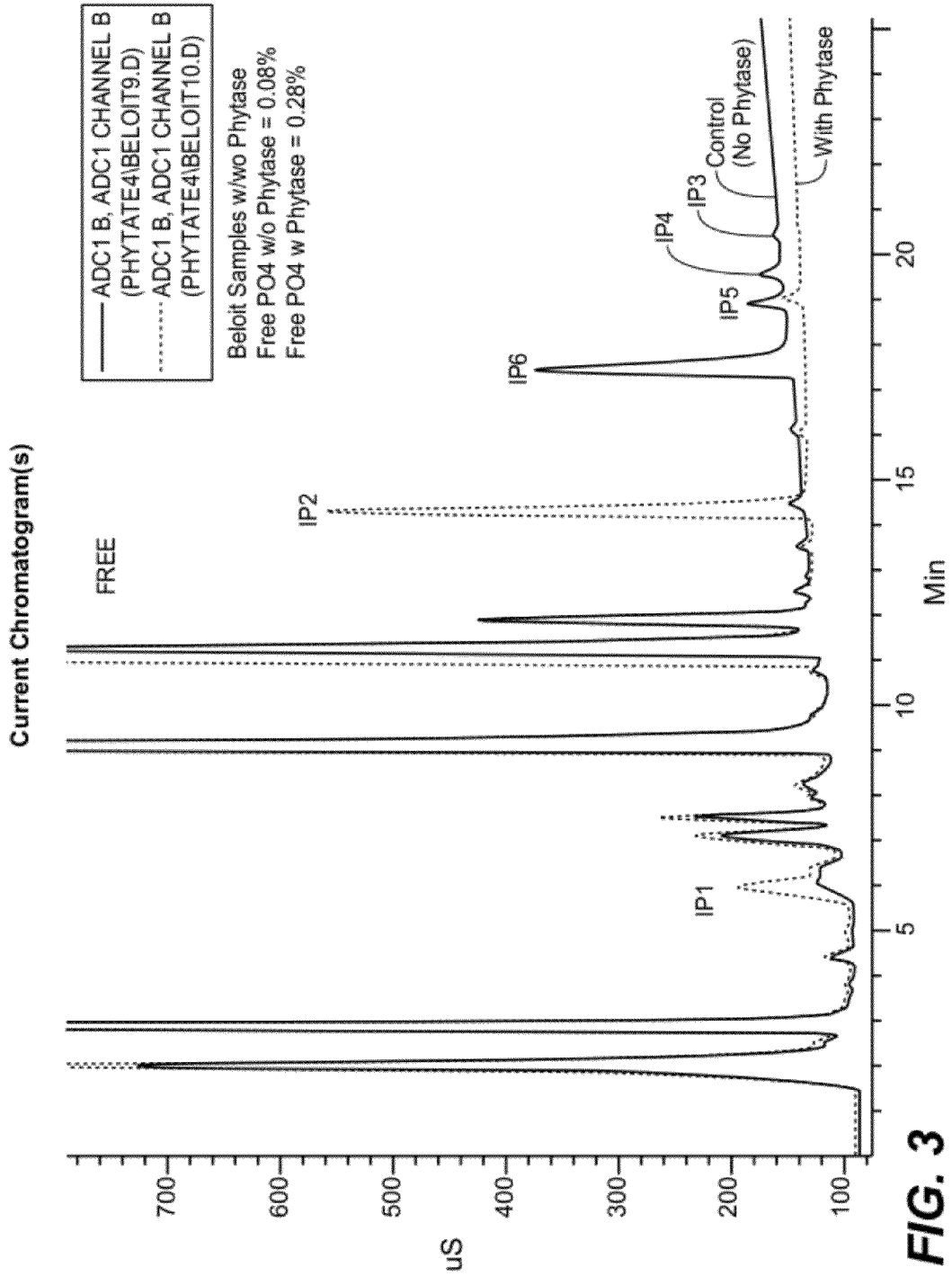
FIG. 3 is a graph showing the effect of phytase addition during liquefaction of whole ground corn on the phytic acid content in DDGS.

As shown in FIG. 3, LC analysis demonstrated that phytic acid (IP6) and the intermediates IP4 and IP3 were completely removed, and the levels of IP5 were substantially reduced, by the inclusion of 4 FTU phytase in the primary liquefaction and 2 FTU phytase in the secondary liquefaction.

Example 2

Increase in Variant *B. licheniformis* Alpha-Amylase Performance Using a Thermostable Phytase Liquefacts from Example 1 was refrigerated for approximately 24 hours prior to fermentation. The DS of each liquefact was 35.2%. The pH was 5.2 and was not adjusted. 325 grams of each liquefact was accurately weighed into beakers. 400 ppm urea was added to each (1.3 mls of a 1:10 dilution), followed by 1 ml of a 20% w/w yeast solution. Glucoamylase (i.e., G Zyme 480 Ethanol obtained from Genencor International, Inc. Palo Alto, Calif., USA) was dosed at 0.325 GAU/g DS. For weight loss measurements approximately 150 grams of each liquefact was quantitatively weighed into 250 ml Erlenmeyer flasks and fitted with rubber stoppers with 18 gauge needles to allow $CO_2$ to escape. An additional 150 grams was weighed into another set of Erlenmeyer flasks for sampling and HPLC analysis. All flasks were placed in a forced air shaker set to 32° C. and 150 rpm. The flasks were weighed periodically during fermentation and the amount of alcohol produced was calculated based on weight loss. The data shown in Table 3 showed that the ethanol rate and yield is not negatively affected by addition of phytase in liquefaction.

TABLE 3

Amount of alcohol produced based on weight loss.

| | | Gallons Ethanol per Bushel Corn | | | | |
|---|---|---|---|---|---|---|
| Ferm | Description | 20 | 28 | 45 | 51 | 60 |
| 1 | 1 AAU + 4 FTU primary, 0.5 AAU Secondary | 1.32 | 1.71 | 2.22 | 2.27 | 2.32 |
| 3 | 1 AAU + 4 FTU Primary, 0.5 AAU + 2 FTU Secondary | 1.36 | 1.77 | 2.29 | 2.34 | 2.40 |
| 5 | 1 AAU primary, 0.5 AAU Secondary: Ctrl | 1.36 | 1.78 | 2.32 | 2.37 | 2.44 |
| 7 | 1 AAU + 4 FTU Primary, 0.5 AAU + 2 FTU Secondary 190° F. | 1.33 | 1.75 | 2.28 | 2.33 | 2.37 |

Example 3

Increase in Variant *B. licheniformis* Alpha-Amylase Performance Using a Thermostable Phytase—Lab Scale Test The benefit of adding a thermostable phytase was demonstrated by using 1 kg scale laboratory equipment. A weighed amount of water (544 grams) was heated to 93-96° C. on a stirring hot plate in a 1 liter stainless steel beaker. The hot liquid was placed into the water bath set at 87.2° C. and continuously stirred while adding ~70% of the previously weighed ground corn. Enzyme was added to the pasting slurry which immediately reduced in viscosity. The remaining ground corn was added and a timer was immediately started. The loss of water due to evaporation was controlled by covering the beaker with a watch glass.

The liquid phase of the laboratory scale slurry included of 35% thin stillage (back set) from a typical dry grind ethanol plant, and 256 grams of ground corn, resulting is 32% DS due to the addition of dry substance present in the thin stillage. The pH of the back set was adjusted to 5.2 with sodium carbonate. A *Bacillus licheniformis* alpha amylase (i.e., SPEZYME® FRED; Genencor) was used at 10 Liquefon Units (LU) per gram of dry substance corn with either 0 FTU, 2 FTU, or 12 FTU of BP 111 phytase added per gram of dry substance corn.

The DE determinations taken at 20 minute intervals are shown in Table 4. The experiment clearly demonstrates that the liquefaction process containing phytase shows improved performance in terms of apparent alpha amylase activity.

TABLE 4

Effect of thermostable phytase on the DE progression during liquefaction of 35% DS whole ground corn.

|  |  | Control | Test 1 | Test 2 |
|---|---|---|---|---|
| SPEZYME FRED | LU/g DS | 10 | 10 | 10 |
| BP 111 | FTU/g DS | 0 | 2 | 12 |
|  | Temperature | 185 | 185 | 185 |
|  | Minutes | DE | DE | DE |
|  | 20 | 5.3 | 4.7 | 5.1 |
|  | 40 | 5.7 | 6.1 | 6.4 |
|  | 60 | 6.9 | 7.2 | 7.6 |
|  | 80.0 | 7.7 | 8.3 | 8.9 |
|  | 100 | 8.3 | 8.9 | 9.9 |
|  | 120 | 8.6 | 10.1 | 11.2 |
|  | 170 | 10.1 | 12.5 | 14.0 |
|  | Slope | 0.030 | 0.050 | 0.059 |

Since the slope of DE development over time correlates with alpha amylase activity, the performance of SPEZYME FRED is improved by 67%, i.e., from 0.03 DE/min to 0.05 DE/min, with the addition of 2 FTU/g phytase of dry substance corn, and improved by 97%, i.e., from 0.03 DE/min to 0.059 DE/min, with 12 FTU/g phytase of dry substance corn.

Example 4

Increase in Truncated *G. stearothermophilus* Alpha-Amylase Performance Using a Thermostable Phytase The liquefaction conditions were as described in Example 2. In this case a *Bacillus stearothermophilus* alpha amylase (SPEZYME® XTRA; Genencor) was used at doses of 1.5 AAU in the simulated hot slurry tank (primary liquefaction) with 0.75 AAU added in the secondary liquefaction. The control contained no phytase and the test sample contained 4 FTU phytase in the hot slurry tank and 2 FTU phytase in the secondary liquefaction. The liquid phase was made up to contain 35% of the weight as thin stillage. The pH was adjusted to pH 5.6 prior to cooking. At the end of liquefaction the pH of a room temperature sample was 5.35. The DE progression during secondary liquefaction is shown in Table 5.

TABLE 5

Effect of thermostable phytase, BP111 on the DE progression during liquefaction of 35% DS whole ground corn.

|  |  | Control | Test | Control | Test |
|---|---|---|---|---|---|
| Hot Slurry Process |  |  |  |  |  |
| SPEZYME XTRA | AAU/g DS | 1.5 | 1.5 | 1.5 | 1.5 |
| BP 111 | FTU/g DS | 0 | 4 | 0 | 4 |
|  | Temperature | 185 | 185 | 185 | 185 |
|  | pH | 5.35 | 5.35 | 5.65 | 5.65 |
|  | Minutes | DE | DE | DE | DE |
|  | 5 | 3.1 | 3.0 | 4.2 | 3.3 |
|  | 10 | 4.2 | 4.0 | 4.3 | 4.1 |
|  | 20 | 5.4 | 5.4 | 5.7 | 5.5 |
| Secondary Liquefaction |  |  |  |  |  |
| SPEZYME XTRA | AAU/g DS | 0.75 | 0.75 | 0.75 | 0.75 |
| BP 111 | FTU/g DS | 0.0 | 2.0 | 0.0 | 2.0 |
|  | Temperature | 185 | 185 | 185 | 185 |

TABLE 5-continued

Effect of thermostable phytase, BP111 on the DE progression during liquefaction of 35% DS whole ground corn.

|  | Control | Test | Control | Test |
|---|---|---|---|---|
| Minutes | DE | DE | DE | DE |
| 5 | 5.16 | 6.67 | 6.44 | 7.51 |
| 20 | 5.87 | 7.80 | 7.67 | 8.64 |
| 40 |  |  | 7.98 | 10.29 |
| 50 | 5.90 | 9.42 |  |  |
| 60 |  |  | 8.32 | 11.28 |
| 80 | 6.32 | 10.58 |  |  |
| 90 |  |  | 8.72 | 11.83 |
| 110 | 6.35 | 11.01 |  |  |
| 120 |  |  | 9.36 | 12.51 |
| 140 | 6.39 | 11.40 |  |  |
| Slope of Secondary DE | 0.005 | 0.029 | 0.017 | 0.036 |

The results show that the addition of BP 111 phytase in the hot slurry resulted in improved performance in the secondary liquefaction step. As shown in Table 5, when the secondary dose of SPEZYME® XTRA is added in the control samples, DE development continues for about 20 minutes after which the alpha amylase appears to become inactivated. However, addition of the phytase prolongs DE development and the overall performance of the amylase.

Because SPEZYME® XTRA was designed for use in a conventional liquefaction process operated at a pH of about 5.8, it does not have optimal stability at the pH of the test run. Therefore, while it is apparent that the addition of the thermostable phytase improved DE development under the test conditions, a comparison of the slopes of DE development in the presence and absence or phytase at do not fully reflect the rate of DE development that can be achieved using optimized thermostable enzymes. To obtain more meaningful slope data, the test was repeated with an initial pH of 5.65-5.70. Under these conditions, the improvement in DE development was about 111% (i.e., a slope change of from 0.017 DE/min to 0.036 DE/min from 60 to 160 minutes during secondary liquefaction). The results at pH 5.65-5.7 pH show the numerical performance improvement of SPEZYME® XTRA with the thermostable phytase at a pH close to its optimum, while the results obtained at pH 5.35 demonstrate that the benefits of the thermostable phytase are observed at a lower pH.

Example 5

Purification of Phytase Enzymes

Purification of phytase enzymes was performed using a 6 His-tag N-terminally fused to the phytase enzymes. *B. subtilis*, transformed with a plasmid coding for the 6 His-tagged phytase enzyme, was cultivated in shake flasks at 37° C. and 160 rpm using standard LB medium with addition of 20 mg/l Neomycin. At this stage, the culture medium accumulated significant amount of phytase activity. About 2 l of the culture broth were adjusted to pH 8.0, filtered and applied to a column packed with 10 ml of Ni-NTA sepharose resin (Qiagen). The column was washed with 50 mM Tris-HCl buffer, 300 mM NaCl, pH 8.0 until OD280 dropped below 0.05. Subsequently the bound phytase was eluted with the same buffer containing 250 mM imidazole hydrochloride. The elutate was dialysed against 50 mM sodium acetate buffer pH 5.0 and stored at 4° C. The enzyme solution was then applied to a Resource S column equilibrated with 20 mM sodium acetate buffer pH 5.0 and the elution was performed using a salt gradient from

Example 6

Phytase Activity Assays

Phytase assays were carried out in microtiter plates. The reaction had a total volume of 100 microliter containing buffer, as described below, 10 mM phytate, 1 mM calcium chloride and 0.05% (w/v) Pluronic F68. The reaction was allowed to proceed for 30 minutes at a given temperature, e.g. between 37° C. and 90° C.

Phosphate liberation from phytate as a measure of the phytase activity was assayed by incubating aliquots of the samples (typically 5 μA in a total volume of 50 μl of phosphate detection assay for 1 h at 37° C. The assay contained the following compounds at the given final concentrations: 1 M Tris/HCl, pH 7.0, 0.01% (v/v) Triton X-100, 0.025 mM ADHP (MoBiTec, Göttingen, Germany), 0.2 μml maltose-phosphorylase, 0.25 mM maltose, 1.25 μml glucose oxidase, 0.25 μml horseradish peroxidase, 1 mM EDTA, 0.35 mg/ml BSA. The reaction was stopped by the addition of 30 μl of 2700 μml catalase in H2O, Subsequently the fluorescence at 595 nm was measured, using 535 nm as excitation wavelength. The amount of phosphate was determined using a calibration curve with phosphate solutions of known concentrations. One enzymatic unit is defined as the liberation of one micromole phosphate per minute.

For assaying phytase activity at different pH values the following buffers were used: 200 mM glycine/HCl from pH 2.0 to pH 3.5 and 100 mM sodium acetate/acetic acid between pH 4.0 and pH 5.5.

Example 7

Specific Activity

The specific activity of BP-WT and variant phytase enzymes was estimated using the purified enzymes according to Example 5. Phytase activity was determined in microtiter plates using a coupled enzymatic assay: Enzyme preparations were diluted in dilution buffer (50 mM sodium acetate, 0.05% Pluronic F-68, 1 mg/ml BSA). An aliquot of the enzyme solution, typically 5 μl to 10 μl was incubated in the phytate assay with a total volume of 80 μl. The assay contains the following buffers, substrates and salts at the given final concentrations: 200 mM sodium acetate, pH 5.5, 10 mM phytate, 1 mM CaCl2, 0.05% (w/v) Pluronic F-68). The assays were incubated for 30 min at 37° C. in the case of the BP-WT phytase and for 30 min at 67° C. or 80° C. in the case of the variant phytase enzymes.

Phosphate liberation from phytate as a measure of the phytase activity was assayed by incubating aliquots of the respective samples (typically 5 μl) in a total volume of 50 μl of phosphate detection assay for 1 h at 37° C. The assay contained the following compounds at the given final concentrations: 1 M Tris/HCl, pH 7.0, 0.01% (v/v) Triton X-100, 0.025 mM ADHP (MoBiTec, Göttingen, Germany), 0.2 U/ml maltosephosphorylase, 0.25 mM maltose, 1.25 U/ml glucose oxidase, 0.25 U/ml horseradish peroxidase, 1 mM EDTA, 0.35 mg/ml BSA. The reaction was stopped by the addition of 30 μl of 2700 μml catalase in H2O, Subsequently the fluorescence at 595 nm was measured, using 535 nm as excitation wavelength. The amount of phosphate was determined using a calibration curve with phosphate solutions of known concentrations. One enzymatic unit is defined as the liberation of one micromole phosphate per minute.

Phytase concentration was calculated from the absorbance of the preparations at 280 nm and the respective extinction coefficient for each of each phytase variant. The extinction coefficients were calculated on the basis of the amino acid composition of the proteins according to a method provided by Gill and von Hippel, Analytical Biochemistry 182:319-326 (1989).

TABLE 6

Specific activity of phytase variants according to BP-WT, SEQ ID NO: 1.
The specific activity of the variant phytase enzymes was determined at
67° C. and 80° C. as described above.
The BP-WT enzyme has a specific activity of 1021 U/mg
at 37° C. under the conditions described above.

| Variant | Specific activity at 67° C./[U/mg] | Specific activity at 80° C./[U/mg] |
|---|---|---|
| N37Y/S75P/A89T/D92A/T134I/H160R/F164E/T171V/ T176K/A178P/S188P/G192A/K198R/K207E/ A209S/S248L/Q256Y/A261E/N270K/A374P [BP-112] | 2381 | 2592 |
| N37Y/G77S/A89T/D92A/T134I/H160R/F164E/T171V/ T176K/A178P/S188P/G192A/K198R/K207E/ A209S/S248L/Q256Y/A261E/N270K/A374P [BP-110] | 2192 | 2315 |
| N37Y/S75P/Q76R/A89T/D92A/T134I/H160R/F164E/ T171I/T176K/A178P/S188P/G192A/K207E/ A209S/A235V/S248L/Q256Y/A261E/N270K/A374P [BP-111] | 2065 | 2052 |
| N37Y/A89T/D92A/T134I/F164E/T171V/T176K/ A178P/G192A/K207E/A209S/A235V/S248L/Q256P/ A261E/N270K/A374P | 1725 | 1652 |
| S75P/Q76R/A89T/D92A/T134I/H160R/F164E/T171I/ T176K/A178P/S188P/G192A/K207E/A209S/ S248L/Q256Y/A261E/N270K/A374P | 1680 | 1481 |
| N37Y/Q76R/A89T/D92A/T134I/H160R/F164E/T171I/ T176K/A178P/S188P/G192A/K207E/A209S/ S248L/Q256Y/A261E/N270K/A374P | 2441 | 1948 |

TABLE 6-continued

Specific activity of phytase variants according to BP-WT, SEQ ID NO: 1.
The specific activity of the variant phytase enzymes was determined at
67° C. and 80° C. as described above.
The BP-WT enzyme has a specific activity of 1021 U/mg
at 37° C. under the conditions described above.

| Variant | Specific activity at 67° C./[U/mg] | Specific activity at 80° C./[U/mg] |
|---|---|---|
| N37Y/Q76R/A89T/D92A/T134I/F164S/T171V/T176K/ A178P/S188P/G192A/K207E/A209S/A235V/ S248L/Q256A/A261E/N270K/A374P | 1613 | 1412 |
| S75P/A89T/D92A/T134I/F164E/T171V/T176K/ A178P/S188P/G192A/K207E/A209S/A235V/S248L/ Q256Y/A261E/N270K/A374P | 2171 | 1820 |
| S75P/Q76R/A89T/D92A/T134I/H160R/F164E/T171V/ T176K/A178P/S188P/G192A/K207E/A209S/ A235V/S248L/Q256Y/A261E/N270K/P367L/ A374P | 2421 | 2038 |
| N37Y/A89T/D92A/T134I/F164E/T171I/T176K/A178P/ G192A/K207E/A209S/A235V/S248L/Q256Y/ A261E/N270K/A374P | 2314 | 1752 |
| N37Y/Q76R/A89T/D92A/T134I/F164E/T171V/T176K/ A178P/G192A/K207E/A209S/S248L/Q256Y/ A261E/N270K/A374P | 2251 | 1783 |
| N37Y/Q76R/A89T/D92A/T134I/F164E/T171V/T176K/ A178P/G192A/K207E/A209S/S248L/Q256A/ A261E/N270K/A374P | 1597 | 1289 |
| N37Y/S75P/Q76R/A89T/D92A/T134I/F164E/T171V/ T176K/A178P/K207E/A209S/A235V/S248L/ Q256A/A261E/N270K/A374P | 1651 | 1104 |
| N37Y/S75P/A89T/D92A/T134I/H160R/F164E/T171V/ T176K/A178P/K207E/A209S/A235V/S248L/ Q256Y/A261E/N270K/A374P | 2378 | 1750 |
| N37Y/A89T/D92A/T134I/H160R/F164S/T171I/T176K/ A178P/S188P/G192A/K207E/A209S/A235V/ S248L/Q256E/A261E/N270K/A374P | 2010 | 1392 |
| A89T/D92A/T134I/H160R/F164E/T171V/T176K/ A178P/G192A/K207E/A209S/A235V/S248L/Q256Y/ A261E/N270K/A374P | 2161 | 1468 |
| N37Y/S75P/A89T/D92A/T134I/H160R/F164S/T171V/ T176K/A178P/S188P/K207E/A209S/S248L/ Q256H/A261E/N270K/A374P | 2421 | 962 |
| N37Y/S75P/A89T/D92A/T134I/F164S/T171V/T176K/ A178P/S188P/G192A/K207E/A209S/S248L/ Q256A/A261E/N270K/A374P | 1866 | 998 |
| S75P/Q76R/A89T/D92A/T134I/H160R/F164E/T171V/ T176K/A178P/G192A/K207E/A209S/S248L/ Q256A/A261E/N270K/A374P | 1755 | 843 |
| N37Y/Q76R/A89T/D92A/T134I/H160R/F164S/T171V/ T176K/A178P/G192A/K207E/A209S/A235V/ S248L/Q256Y/A261E/N270K/A374P | 2476 | 1654 |

Example 8

Generation and Characterization of Phytase Variants

Phytase variants were generated using different methods for the mutagenesis of the DNA encoding the phytase proteins like cassette or PCR mutagenesis or other mutagenesis methods well known in the art. Those methods comprise the ones listed above such as the methods disclosed in Morinaga et al., *Biotechnology* 2:646-649 (1984); in Nelson and Long, *Analytical Biochemistry* 180:147-151 (1989); or the Error Threshold Mutagenesis protocol described in WO 92/18645. For mutagenic PCR another suitable method is disclosed by Cadwell and Joyce, *PCR Methods Appl.* 3:136-140 (1994).

Phytase variants were heterologously expressed in one or more of the following expression hosts: *Saccharomyces cerevisiae, Bacillus subtilis, Escherichia coli.*

Example 9

Thermal Stability

The thermal stability of phytase variants was characterized by their inactivation temperature. The inactivation temperature was determined by the residual activity of the phytase enzymes after incubation for 10 min at different temperatures, pH 5.5 and subsequent incubation at 37° C. for 60 min. Residual activities were determined measuring phytase activities for 60 min at pH 3.5 and 37° C. The inactivation temperature is defined as the temperature at which the residual activity is 50% compared to the residual activity after incubation for the same duration under the same conditions at room temperature. Where appropriate extrapolations and interpolations from the activity data were made in order to determine the temperature corresponding to 50% residual activity. Thermal stability differences (TD) in [° C.] were calculated by subtracting the inactivation temperatures of two enzymes from each other.

TABLE 7

Thermal stability of phytase variants according to BT-WT, SEQ ID NO: 1. Improvements in thermal stability are presented as thermal stability differences TD between variant and wild-type (BP-WT) phytase enzyme, i.e. TD = (inactivation temperature of the variant phytase) − (inactivation temperature of BP-WT).

| Variant | TD/[° C.] |
|---|---|
| N37Y/S75P/A89T/D92A/T134I/H160R/F164E/T171V/T176K/A178P/S188P/G192A/K198R/K207E/A209S/S248L/Q256Y/A261E/N270K/A374P [BP-112] | 26.5 |
| N37Y/G77S/A89T/D92A/T134I/H160R/F164E/T171V/T176K/A178P/S188P/G192A/K198R/K207E/A209S/S248L/Q256Y/A261E/N270K/A374P [BP-110] | 25.9 |
| N37Y/S75P/Q76R/A89T/D92A/T134I/H160R/F164E/T171I/T176K/A178P/S188P/G192A/K207E/A209S/A235V/S248L/Q256Y/A261E/N270K/A374P [BP-111] | 26.8 |
| N37Y/A89T/D92A/T134I/F164E/T171V/T176K/A178P/G192A/K207E/A209S/A235V/S248L/Q256P/A261E/N270K/A374P | 23.7 |
| S75P/Q76R/A89T/D92A/T134I/H160R/F164E/T171I/T176K/A178P/S188P/G192A/K207E/A209S/S248L/Q256Y/A261E/N270K/A374P | 24.2 |
| N37Y/Q76R/A89T/D92A/T134I/H160R/F164E/T171I/T176K/A178P/S188P/G192A/K207E/A209S/S248L/Q256Y/A261E/N270K/A374P | 25.0 |
| N37Y/Q76R/A89T/D92A/T134I/F164S/T171V/T176K/A178P/S188P/G192A/K207E/A209S/A235V/S248L/Q256A/A261E/N270K/A374P | 22.6 |
| S75P/A89T/D92A/T134I/F164E/T171V/T176K/A178P/S188P/G192A/K207E/A209S/A235V/S248L/Q256Y/A261E/N270K/A374P | 24.9 |
| S75P/Q76R/A89T/D92A/T134I/H160R/F164E/T171V/T176K/A178P/S188P/G192A/K207E/A209S/A235V/S248L/Q256Y/A261E/N270K/P367L/A374P | 24.1 |
| N37Y/A89T/D92A/T134I/F164E/T171I/T176K/A178P/G192A/K207E/A209S/A235V/S248L/Q256Y/A261E/N270K/A374P | 23.4 |
| N37Y/Q76R/A89T/D92A/T134I/F164E/T171V/T176K/A178P/G192A/K207E/A209S/S248L/Q256Y/A261E/N270K/A374P | 23.5 |
| N37Y/Q76R/A89T/D92A/T134I/F164E/T171V/T176K/A178P/G192A/K207E/A209S/S248L/Q256A/A261E/N270K/A374P | 24.4 |
| N37Y/S75P/Q76R/A89T/D92A/T134I/F164E/T171V/T176K/A178P/K207E/A209S/A235V/S248L/Q256A/A261E/N270K/A374P | 22.4 |
| A89T/D92A/T134I/H160R/F164E/T171V/T176K/A178P/G192A/K207E/A209S/A235V/S248L/Q256Y/A261E/N270K/A374P | 23.5 |
| S75P/Q76R/A89T/D92A/T134I/H160R/F164E/T171V/T176K/A178P/G192A/K207E/A209S/S248L/Q256A/A261E/N270K/A374P | 22.9 |

TABLE 8

Thermal activity differences (TAD) of phytase variants according to BT-WT, SEQ ID NO: 1. Improvements in thermal activity are given as T50 differences between variant and wild-type (BP-WT) phytase enzyme, i.e. TAD = T50(variant phytase) − T50(BP-WT).

| Variant | TAD/[° C.] |
|---|---|
| N37Y/S75P/A89T/D92A/T134I/H160R/F164E/T171V/T176K/A178P/S188P/G192A/K198R/K207E/A209S/S248L/Q256Y/A261E/N270K/A374P [BP-112] | 20.2 |
| N37Y/G77S/A89T/D92A/T134I/H160R/F164E/T171V/T176K/A178P/S188P/G192A/K198R/K207E/A209S/S248L/Q256Y/A261E/N270K/A374P [BP-110] | 20.0 |
| N37Y/S75P/Q76R/A89T/D92A/T134I/H160R/F164E/T171I/T176K/A178P/S188P/G192A/K207E/A209S/A235V/S248L/Q256Y/A261E/N270K/A374P [BP-111] | 20.1 |
| N37Y/A89T/D92A/T134I/F164E/T171V/T176K/A178P/G192A/K207E/A209S/A235V/S248P/Q256P/A261E/N270K/A374P | 19.5 |
| S75P/Q76R/A89T/D92A/T134I/H160R/F164E/T171I/T176K/A178P/S188P/G192A/K207E/A209S/S248L/Q256Y/A261E/N270K/A374P | 19.3 |
| N37Y/Q76R/A89T/D92A/T134I/H160R/F164E/T171I/T176K/A178P/S188P/G192A/K207E/A209S/S248L/Q256Y/A261E/N270K/A374P | 19.3 |
| N37Y/Q76R/A89T/D92A/T134I/F164S/T171V/T176K/A178P/S188P/G192A/K207E/A209S/A235V/S248L/Q256A/A261E/N270K/A374P | 18.9 |
| S75P/A89T/D92A/T134I/F164E/T171V/T176K/A178P/S188P/G192A/K207E/A209S/A235V/S248L/Q256Y/A261E/N270K/A374P | 19.0 |
| S75P/Q76R/A89T/D92A/T134I/H160R/F164E/T171V/T176K/A178P/S188P/G192A/K207E/A209S/A235V/S248L/Q256Y/A261E/N270K/P367L/A374P | 18.9 |
| N37Y/A89T/D92A/T134I/F164E/T171I/T176K/A178P/G192A/K207E/A209S/A235V/S248L/Q256Y/A261E/N270K/A374P | 18.8 |
| N37Y/Q76R/A89T/D92A/T134I/F164E/T171V/T176K/A178P/G192A/K207E/A209S/S248L/Q256Y/A261E/N270K/A374P | 18.7 |
| N37Y/Q76R/A89T/D92A/T134I/F164E/T171V/T176K/A178P/G192A/K207E/A209S/S248L/Q256A/A261E/N270K/A374P | 18.9 |
| N37Y/S75P/Q76R/A89T/D92A/T134I/F164E/T171V/T176K/A178P/K207E/A209S/A235V/S248L/Q256A/A261E/N270K/A374P | 18.4 |
| N37Y/S75P/A89T/D92A/T134I/H160R/F164E/T171V/T176K/A178P/K207E/A209S/A235V/S248L/Q256Y/A261E/N270K/A374P | 17.9 |
| N37Y/A89T/D92A/T134I/H160R/F164S/T171I/T176K/A178P/S188P/G192A/K207E/A209S/A235V/S248L/Q256E/A261E/N270K/A374P | 17.9 |
| A89T/D92A/T134I/H160R/F164E/T171V/T176K/A178P/G192A/K207E/A209S/A235V/S248L/Q256Y/A261E/N270K/A374P | 17.8 |
| N37Y/S75P/A89T/D92A/T134I/F164S/T171V/T176K/A178P/S188P/K207E/A209S/S248L/Q256H/A261E/N270K/A374P | 17.8 |
| N37Y/S75P/A89T/D92A/T134I/F164S/T171V/T176K/A178P/S188P/G192A/K207E/A209S/S248L/Q256A/A261E/N270K/A374P | 17.4 |
| S75P/Q76R/A89T/D92A/T134I/H160R/F164E/T171V/T176K/A178P/G192A/K207E/A209S/S248L/Q256A/A261E/N270K/A374P | 17.5 |
| N37Y/Q76R/A89T/D92A/T134I/H160R/F164S/T171V/T176K/A178P/G192A/K207E/A209S/A235V/S248L/Q256Y/A261E/N270K/A374P | 17.6 |

Example 10

Thermal Activity

The thermal activity of phytase variants was characterized by their temperature-activity profile. As a measure of the temperature-activity profile the value T50 was defined, at which the total enzymatic turnover of the substrate is 50% compared to the total enzymatic turnover of the substrate in a reaction running essentially under the same conditions but at the temperature optimum of the phytase variant. The temperature-activity profiles were determined by incubation of the phytase enzymes at pH 5.5 and various temperatures under conditions further described in Example 6. T50 values were determined by appropriate interpolations and extrapolations from the experimental data. Thermal activity differences (TAD) in [° C.] were calculated by subtracting the T50 values of two enzymes from each other.

Example 11

Properties Overview of Phytase Variants

Table 4 summarizes the properties specific activity, thermal stability and thermal activity of phytase variants that were before presented in Examples 7-9.

TABLE 9

Specific activity, thermal stability and thermal activity of different phytase variants according to BT-WT, SEQ ID NO: 1. Values for specific activities, thermal stability (TD), and thermal activity (TAD) were derived as described in Example 7, Example 8, and Example 9, respectively.

| Variant | TD/[° C.] | TAD/[° C.] | Specific activity at 67° C./ [U/mg] | Specific activity at 80° C./ [U/mg] |
|---|---|---|---|---|
| N37Y/S75P/A89T/D92A/T134I/H160R/ F164E/T171V/T176K/A178P/S188P/ G192A/K198R/K207E/A209S/S248L/ Q256Y/A261E/N270K/A374P [BP-112] | 26.5 | 20.2 | 2381 | 2592 |
| N37Y/G77S/A89T/D92A/T134I/H160R/ F164E/T171V/T176K/A178P/S188P/ G192A/K198R/K207E/A209S/S248L/ Q256Y/A261E/N270K/A374P [BP-110] | 25.9 | 20.0 | 2192 | 2315 |
| N37Y/S75P/Q76R/A89T/D92A/T134I/ H160R/F164E/T171I/T176K/A178P/ S188P/G192A/K207E/A209S/A235V/ S248L/Q256Y/A261E/N270K/A374P [BP-110] | 26.8 | 20.1 | 2065 | 2052 |
| N37Y/A89T/D92A/T134I/F164E/T171V/ T176K/A178P/G192A/K207E/A209S/ A235V/S248L/Q256P/A261E/N270K/ A374P | 23.7 | 19.5 | 1725 | 1652 |
| S75P/Q76R/A89T/D92A/T134I/H160R/ F164E/T171I/T176K/A178P/S188P/ G192A/K207E/A209S/S248L/Q256Y/ A261E/N270K/A374P | 24.2 | 19.3 | 1680 | 1481 |
| N37Y/Q76R/A89T/D92A/T134I/H160R/ F164E/T171I/T176K/A178P/S188P/ G192A/K207E/A209S/S248L/Q256Y/ A261E/N270K/A374P | 25.0 | 19.3 | 2441 | 1948 |
| N37Y/Q76R/A89T/D92A/T134I/F164S/ T171V/T176K/A178P/S188P/G192A/ K207E/A209S/A235V/S248L/Q256A/ A261E/N270K/A374P | 22.6 | 18.9 | 1613 | 1412 |
| S75P/A89T/D92A/T134I/F164E/T171V/ T176K/A178P/S188P/G192A/K207E/ A209S/A235V/S248L/Q256Y/A261E/ N270K/A374P | 24.9 | 19.0 | 2171 | 1820 |
| S75P/Q76R/A89T/D92A/T134I/H160R/ F164E/T171V/T176K/A178P/S188P/ G192A/K207E/A209S/A235V/S248L/ Q256Y/A261E/N270K/P367L/A374P | 24.1 | 18.9 | 2421 | 2038 |
| N37Y/A89T/D92A/T134I/F164E/T171I/ T176K/A178P/G192A/K207E/A209S/ A235V/S248L/Q256Y/A261E/N270K/ A374P | 23.4 | 18.8 | 2314 | 1752 |
| N37Y/Q76R/A89T/D92A/T134I/F164E/ T171V/T176K/A178P/G192A/K207E/ A209S/S248L/Q256Y/A261E/N270K/ A374P | 23.5 | 18.7 | 2251 | 1783 |
| N37Y/Q76R/A89T/D92A/T134I/F164E/ T171V/T176K/A178P/G192A/K207E/ A209S/S248L/Q256A/A261E/N270K/ A374P | 24.4 | 18.9 | 1597 | 1289 |
| N37Y/S75P/Q76R/A89T/D92A/T134I/ F164E/T171V/T176K/A178P/K207E/ A209S/A235V/S248L/Q256A/A261E/ N270K/A374P | 22.4 | 18.4 | 1651 | 1104 |
| N37Y/S75P/A89T/D92A/T134I/H160R/ F164E/T171V/T176K/A178P/K207E/ A209S/A235V/S248L/Q256Y/A261E/ N270K/A374P | n.d. | 17.9 | 2378 | 1750 |
| N37Y/A89T/D92A/T134I/H160R/F164S/ T171I/T176K/A178P/S188P/G192A/ K207E/A209S/A235V/S248L/Q256E/ A261E/N270K/A374P | n.d. | 17.9 | 2010 | 1392 |
| A89T/D92A/T134I/H160R/F164E/T171V/ T176K/A178P/G192A/K207E/A209S/ A235V/S248L/Q256Y/A261E/N270K/ A374P | 23.5 | 17.8 | 2161 | 1468 |

TABLE 9-continued

Specific activity, thermal stability and thermal activity of different phytase
variants according to BT-WT, SEQ ID NO: 1. Values for specific activities, thermal
stability (TD), and thermal activity (TAD) were derived as described in Example 7,
Example 8, and Example 9, respectively.

| Variant | TD/[° C.] | TAD/[° C.] | Specific activity at 67° C./ [U/mg] | Specific activity at 80° C./ [U/mg] |
|---|---|---|---|---|
| N37Y/S75P/A89T/D92A/T134I/H160R/ F164S/T171V/T176K/A178P/S188P/ K207E/A209S/S248L/Q256H/A261E/ N270K/A374P | n.d. | 17.8 | 2421 | 962 |
| N37Y/S75P/A89T/D92A/T134I/F164S/ T171V/T176K/A178P/S188P/G192A/ K207E/A209S/S248L/Q256A/A261E/ N270K/A374P | n.d. | 17.4 | 1866 | 998 |
| S75P/Q76R/A89T/D92A/T134I/H160R/ F164E/T171V/T176K/A178P/G192A/ K207E/A209S/S248L/Q256A/A261E/ N270K/A374P | 22.9 | 17.5 | 1755 | 843 |
| N37Y/Q76R/A89T/D92A/T134I/H160R/ F164S/T171V/T176K/A178P/G192A/ K207E/A209S/A235V/S248L/Q256Y/ A261E/N270K/A374P | n.d. | 17.6 | 2476 | 1654 |

Example 12

Phytic Acid Hydrolysis in a Liquefact

A. Phytic Acid Determination

Phytic acid content: Phytic acid was extracted from a sample by adjusting the pH of the 5% slurry (if it is dry sample) to pH 10 and then determined by an HPLC method using an ion exchange column. Phytic acid was eluted from the column using a NaOH gradient system. Phytic acid content in the liquid was then calculated by comparing to a phytic acid standard.

B. Results

Figure 5:
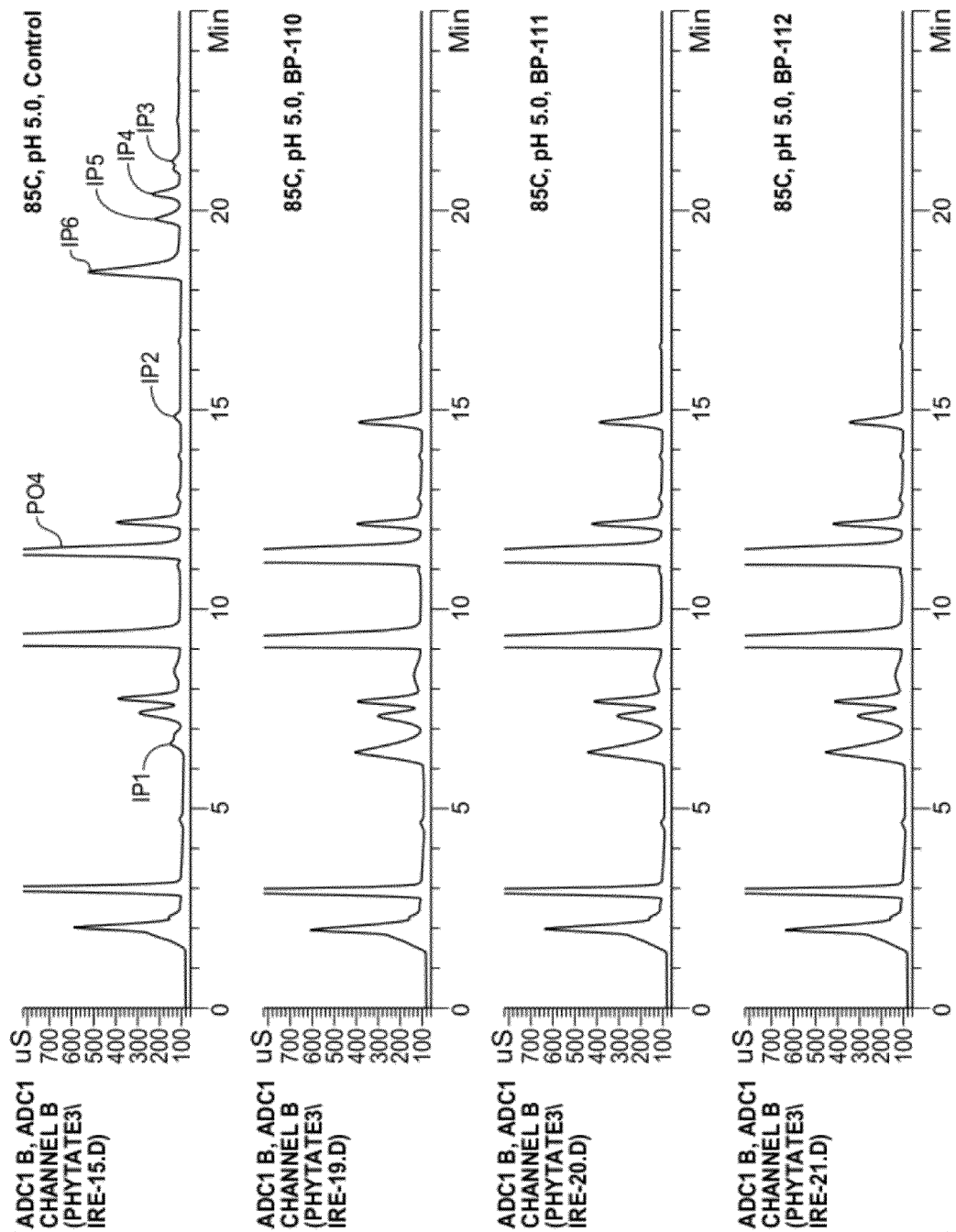
FIGS. 5 and 6 show the hydrolysis of phytate by thermostable phytases under liquefaction conditions.
Figure 6:
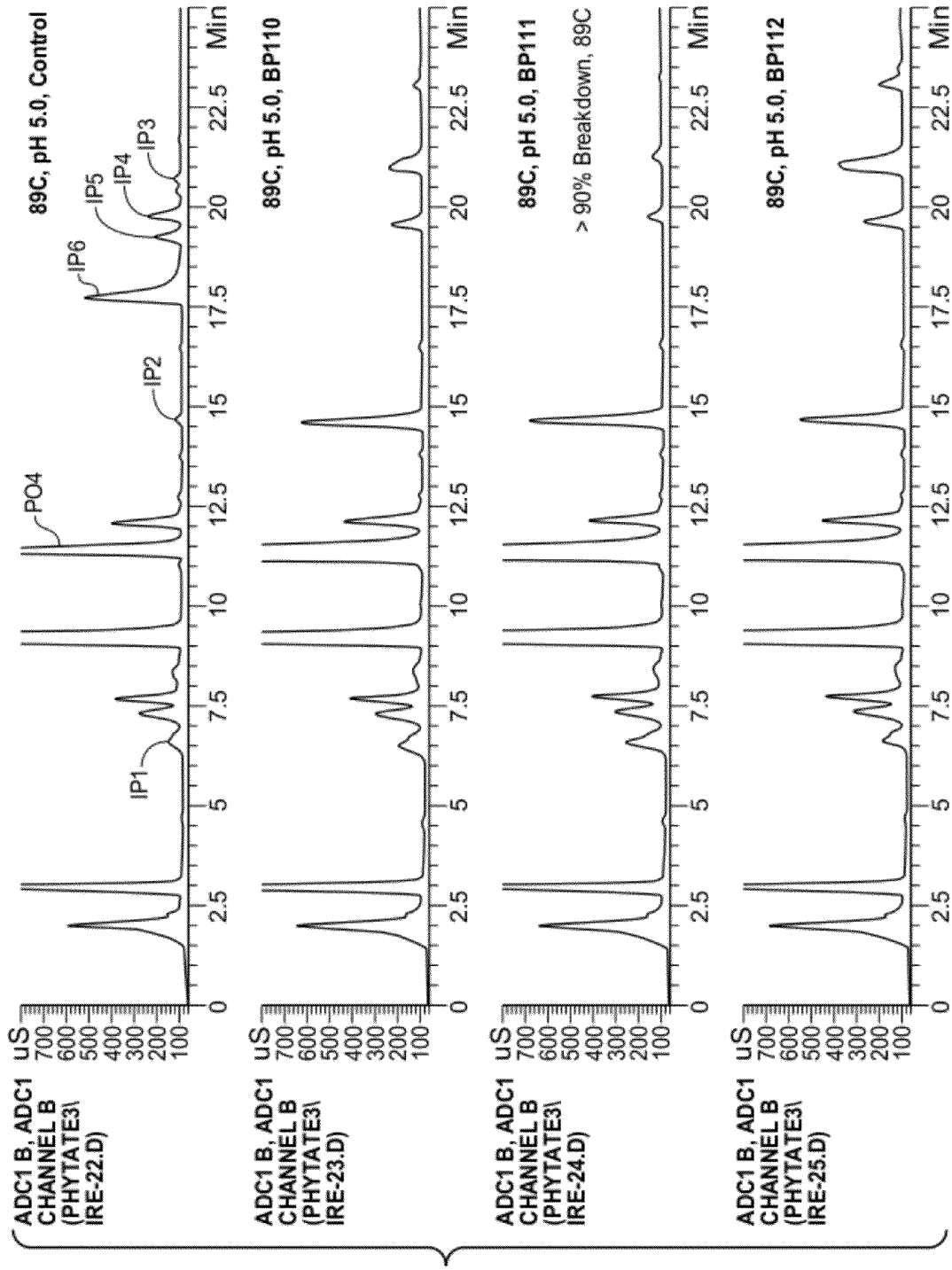

The effect of temperature on the hydrolysis of phytic acid of the whole ground corn liquefact from a conventional dry grind liquefaction process (source: Illinois River Energy, Monroe, Ill.) by different thermostable BP variant phytase, i.e., BP110, BP111 and BP112 was studied. The pH of a 32% ds ("dry solid") whole ground corn ds corn liquefact was adjusted to pH 5.0. and placed in a water bath maintained at 85° C. and 89° C. After temperature equilibration, BP-phytase was added at 4.0 FTU/gds. corn. Samples were then taken at 20 minutes and the enzyme reaction was terminated by the addition of 10 mM sodium hydroxide (diluted 1 to 10 fold). The diluted samples were then filtered and analyzed by HPLC for their phytate derivatives profile (IP1 to IP6). The HPLC chromatograms in FIGS. 15 and 16 clearly showed that phytase from all three variants catalyzed the hydrolysis of phytic acid at temperature greater than 85° C. The phytic acid content (phytic acid (IP6) and intermediates IP1 to IP5) in whole ground corn liquefact is around 1.7% ds corn and data in FIG. 5 showed that more than 95% of the phytic acid was hydrolyzed by thermostable phytase under the current liquefaction conditions. Significantly, the HPLC profile from the samples incubated at 89° C. showed that the BP-111 phytase variant exhibited higher thermostability compared to phytase from two other variants (see FIG. 6; BP-110 and BP-112).

Example 13

Increase in Thermostability of Variant G. stearothermophilus Alpha-Amylase Using a Thermostable Phytase Facilitates a Single Alpha-Amylase Dose System in Liquefaction Systems Using Jet Cookers A series of experiments were performed to determine if the presence of a thermostable phytase could increase the robustness and thermostability of a commercially available alpha-amylase without adjusting the pH of the slurry as required using conventional compositions and methods. The experiments were carried out using 32% ds ground corn, with thin stillage making up 35% of the liquid phase. 81.9 kilograms of liquid adjusted to pH 4.8 was heated to 196° F. and 24 kilograms of ground corn was added. Note that in this experiment the pH of the slurry was lowered to pH 4.8 to simulate the low pH conditions of the cook water, not raised as would be necessary to stabilize an alpha-amylase in a conventional process.

The enzyme(s) were added and the remaining 24 kilograms of corn was added. After 20 minutes of hydrolysis at 180-182° F., the hot slurry was pumped at 6.3 liters/min through a steam injection cooker, known in the industry as Hydrothermal brand model M 103. Three different jet temperatures were tested for studying the thermostability of alpha-amylase (ie. 225, 220 and 215° F.). This temperature was maintained for 4.5-5 minutes by holding in delay loops equipped with a back pressure valve maintained at ~20 psi. The material exiting the system was allowed to flash to atmospheric pressure and samples were collected for performing secondary liquefaction at 185° F.

The jet cook temperature, dose and sampling scheme is shown in Table 10. The exemplary alpha-amylase was GC 358 (a variant of G. stearothermophilus alpha-amylase including the substitution S242Q). The dose is given in AAU/g DS corn. The exemplary thermostable phytase was BP 111 (SEQ ID NO: 3). The dose is given in FTU/g DS corn. Dextrose equivalents (DE) measured at various intervals following secondary liquefaction are shown in Table 11.

TABLE 10

Dosing and sampling.

| Test | Hot slurry Temp (° F.) | Jet Temp (° F.) | Primary Dose GC358 | Primary Dose BP111 | Secondary Dose GC358 | Secondary Dose BP111 | Secondary Temp (° F.) |
|---|---|---|---|---|---|---|---|
| Trial 1 | 180-182 | 225 | 1.6 | 2 | 0 | 0 | 185 |
| Trial 2 | 180-182 | 220 | 1.6 | 2 | 0 | 0 | 185 |
| Trial 3 | 180-182 | 215 | 1.6 | 2 | 0 | 0 | 185 |

The DE development shown in Table 11 is evidence of alpha-amylase activity, and is herein referred to as apparent alpha-amylase activity. The 20-minute treatment with thermostable phytase clearly resulted in an increase in apparent alpha-amylase thermostability presumably due to the removal of phytic acid. The DE progression continues in secondary liquefaction with 0.04 DE/min even with no secondary dosage addition after the jet cook. The alpha-amylase activity, as indicated by consistent DE progression, survived after being pumped through jet cooker at three jet temperatures of 225, 220 and 215° F. in three tests.

TABLE 11

DE Progression with time in slurry and secondary liquefaction (pH 5.2, 185° F.) without any secondary dose addition of alpha-amylase or phytase.

| | Hot Slurry | | Secondary Liquefaction Minutes | | | | | | | |
|---|---|---|---|---|---|---|---|---|---|---|
| | 12 | 20 | 27 | 30 | 40 | 50 | 60 | 90 | 120 | 150 |
| Trial 1 | 3.23 | 4.73 | 5.57 | 5.23 | 6.11 | 6.63 | 6.89 | | 9.54 | 10.62 |
| Trial 2 | 3.23 | 4.73 | 5.57 | 5.67 | 5.72 | 6.29 | 7.12 | 8.25 | 9.59 | 10.47 |
| Trial 3 | 3.23 | 4.73 | 5.57 | 5.06 | 5.4 | 6.31 | 7.08 | 8.41 | 9.67 | 10.57 |

What is claimed is:

1. A method for performing starch liquefaction in a slurry that includes granular starch and phytate, the method comprising:
   (a) preparing a slurry comprising granular starch and thin stillage,
   (b) contacting the slurry with a thermostable phytase and a thermostable alpha-amylase, wherein the thermostable phytase comprises at least one amino acid substitution selected from N37Y, H160R and A374P according to the sequence set forth in SEQ ID NO:1,
   (c) performing primary liquefaction and secondary liquefaction, and
   (d) using dextrins produced in step (c) for fermentation, wherein the pH of the slurry is not adjusted in any of steps (a)-(d).

2. The method of claim 1, wherein the slurry does not require a phytase pretreatment step prior to primary liquefaction.

3. The method of claim 1, wherein the thermostable phytase and thermostable alpha-amylase are added at a temperature of 75° C. or higher.

4. The method of claim 1, wherein the thermostable phytase and thermostable alpha-amylase are added at a temperature of 80° C. or higher.

5. The method of claim 1, wherein the thermostable phytase and thermostable alpha-amylase are added at a temperature of 85° C. or higher.

6. The method of claim 1, wherein the slurry does not require the addition of an anti-oxidant.

7. The method of claim 1, wherein the phytase is a recombinant thermostable phytase derived from a *Buttiauxella* spp. phytase.

8. The method of claim 7, wherein the phytase is selected from BP-110 (SEQ ID NO: 3), BPA 11 (SEQ ID NO: 4), and BP-112 (SEQ ID NO: 5).

9. The method of claim 8, wherein the phytase is BP-111 (SEQ ID NO: 4).

10. The method of claim 1, wherein the alpha-amylase is derived from *Bacillus licheniformis* or *Geobacillus stearothermophilus*.

* * * * *

UNITED STATES PATENT AND TRADEMARK OFFICE
CERTIFICATE OF CORRECTION

PATENT NO. : 8,361,755 B2  
APPLICATION NO. : 12/753811  
DATED : January 29, 2013  
INVENTOR(S) : Suzanne Breneman et al.

Page 1 of 1

It is certified that error appears in the above-identified patent and that said Letters Patent is hereby corrected as shown below:

In the Claims:

At column 42, please correct claim 8, line 23 as follows:

8. The method of claim 7, wherein the phytase is selected from BP-110 (SEQ ID NO: 3), ~~BPA-11~~ BP-111 (SEQ ID NO: 4), and BP-112 (SEQ ID NO: 5).

Signed and Sealed this  
Twenty-third Day of September, 2014

Michelle K. Lee  
*Deputy Director of the United States Patent and Trademark Office*

```
                        SEQUENCE LISTING

<160> NUMBER OF SEQ ID NOS: 5

<210> SEQ ID NO 1
<211> LENGTH: 413
<212> TYPE: PRT
<213> ORGANISM: Buttiauxella sp.
<220> FEATURE:
<221> NAME/KEY: misc_feature
<223> OTHER INFORMATION: WT

<400> SEQUENCE: 1

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140
```

```
Ala Val Glu Lys Glu Ala Gln Thr Pro Ile Asp Asn Leu Asn Gln His
145                 150                 155                 160

Tyr Ile Pro Phe Leu Ala Leu Met Asn Thr Val Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
                260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
            355                 360                 365

Ser Leu Asn Gln Pro Ala Gly Ser Val Gln Leu Lys Ile Pro Gly Cys
        370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 2
<211> LENGTH: 413
<212> TYPE: PRT
<213> ORGANISM: Buttiauxella sp.
<220> FEATURE:
<221> NAME/KEY: misc_feature
<223> OTHER INFORMATION: BP-17

<400> SEQUENCE: 2

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95
```

```
Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Val Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 3
<211> LENGTH: 413
<212> TYPE: PRT
<213> ORGANISM: Buttiauxella sp.
<220> FEATURE:
<221> NAME/KEY: misc_feature
<223> OTHER INFORMATION: BP-110

<400> SEQUENCE: 3

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Lys Leu Gly Tyr
        35                  40                  45
```

```
Ile Thr Pro Arg Gly Glu His Leu Ile Ser Leu Met Gly Gly Phe Tyr
 50                  55                  60

Arg Gln Lys Phe Gln Gln Gly Ile Leu Ser Gln Ser Ser Cys Pro
 65                  70                  75                  80

Thr Pro Asn Ser Ile Tyr Val Trp Thr Asp Val Ala Gln Arg Thr Leu
                 85                  90                  95

Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
        130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Val Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Arg Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Pro Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

<210> SEQ ID NO 4
<211> LENGTH: 413
<212> TYPE: PRT
<213> ORGANISM: Buttiauxella sp.
<220> FEATURE:
<221> NAME/KEY: misc_feature
<223> OTHER INFORMATION: BP-111

<400> SEQUENCE: 4

```
Asn Asp Thr Pro Ala Ser Gly Tyr Gln Val Glu Lys Val Ile Leu
1               5                   10                  15

Ser Arg His Gly Val Arg Ala Pro Thr Lys Met Thr Gln Thr Met Arg
            20                  25                  30

Asp Val Thr Pro Tyr Thr Trp Pro Glu Trp Pro Val Lys Leu Gly Tyr
                35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Pro Arg Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
            130                 135                 140

Ala Val Glu Lys Glu Ala Gln Thr Pro Ile Asp Asn Leu Asn Gln Arg
145                 150                 155                 160

Tyr Ile Pro Glu Leu Ala Leu Met Asn Thr Val Leu Asn Phe Ser Lys
                165                 170                 175

Ser Pro Trp Cys Gln Lys His Ser Ala Asp Lys Pro Cys Asp Leu Ala
            180                 185                 190

Leu Ser Met Pro Ser Lys Leu Ser Ile Lys Asp Asn Gly Asn Glu Val
    195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Val Ala Trp Gly Asn Ile
225                 230                 235                 240

His Ser Glu Gln Glu Trp Ala Leu Leu Leu Lys Leu His Asn Val Tyr
            245                 250                 255

Phe Asp Leu Met Glu Arg Thr Pro Tyr Ile Ala Arg His Lys Gly Thr
                260                 265                 270

Pro Leu Leu Gln Ala Ile Ser Asn Ala Leu Asn Pro Asn Ala Thr Glu
    275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
            355                 360                 365

Ser Leu Asn Gln Pro Pro Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

```
<210> SEQ ID NO 5
<211> LENGTH: 413
<212> TYPE: PRT
<213> ORGANISM: Buttiauxella sp.
<220> FEATURE:
<221> NAME/KEY: misc_feature
<223> OTHER INFORMATION: BP-112

<400> SEQUENCE: 5
```

| Asn | Asp | Thr | Pro | Ala | Ser | Gly | Tyr | Gln | Val | Glu | Lys | Val | Ile | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Ser | Arg | His | Gly | Val | Arg | Ala | Pro | Thr | Lys | Met | Thr | Gln | Thr | Met | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Val | Thr | Pro | Tyr | Thr | Trp | Pro | Glu | Trp | Pro | Val | Lys | Leu | Gly | Tyr |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Ile | Thr | Pro | Arg | Gly | Glu | His | Leu | Ile | Ser | Leu | Met | Gly | Gly | Phe | Tyr |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Arg | Gln | Lys | Phe | Gln | Gln | Gly | Ile | Leu | Pro | Gln | Gly | Ser | Cys | Pro |
|-----|-----|-----|-----|-----|-----|-----|-----|-----|-----|-----|-----|-----|-----|-----|
| 65  |     |     |     | 70  |     |     |     |     | 75  |     |     |     |     | 80  |

| Thr | Pro | Asn | Ser | Ile | Tyr | Val | Trp | Thr | Asp | Val | Ala | Gln | Arg | Thr | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Lys | Thr | Gly | Glu | Ala | Phe | Leu | Ala | Gly | Leu | Ala | Pro | Gln | Cys | Gly | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Ile | His | His | Gln | Gln | Asn | Leu | Glu | Lys | Ala | Asp | Pro | Leu | Phe | His |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Pro | Val | Lys | Ala | Gly | Ile | Cys | Ser | Met | Asp | Lys | Thr | Gln | Val | Gln | Gln |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Val | Glu | Lys | Glu | Ala | Gln | Thr | Pro | Ile | Asp | Asn | Leu | Asn | Gln | Arg |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Tyr | Ile | Pro | Glu | Leu | Ala | Leu | Met | Asn | Thr | Val | Leu | Asn | Phe | Ser | Lys |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ser | Pro | Trp | Cys | Gln | Lys | His | Ser | Ala | Asp | Lys | Pro | Cys | Asp | Leu | Ala |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Leu | Ser | Met | Pro | Ser | Arg | Leu | Ser | Ile | Lys | Asp | Asn | Gly | Asn | Glu | Val |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Ser | Leu | Asp | Gly | Ala | Ile | Gly | Leu | Ser | Ser | Thr | Leu | Ala | Glu | Ile | Phe |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Leu | Leu | Glu | Tyr | Ala | Gln | Gly | Met | Pro | Gln | Ala | Ala | Trp | Gly | Asn | Ile |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| His | Ser | Glu | Gln | Glu | Trp | Ala | Leu | Leu | Leu | Lys | Leu | His | Asn | Val | Tyr |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Phe | Asp | Leu | Met | Glu | Arg | Thr | Pro | Tyr | Ile | Ala | Arg | His | Lys | Gly | Thr |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Pro | Leu | Leu | Gln | Ala | Ile | Ser | Asn | Ala | Leu | Asn | Pro | Asn | Ala | Thr | Glu |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ser | Lys | Leu | Pro | Asp | Ile | Ser | Pro | Asp | Asn | Lys | Ile | Leu | Phe | Ile | Ala |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Gly | His | Asp | Thr | Asn | Ile | Ala | Asn | Ile | Ala | Gly | Met | Leu | Asn | Met | Arg |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Trp | Thr | Leu | Pro | Gly | Gln | Pro | Asp | Asn | Thr | Pro | Pro | Gly | Gly | Ala | Leu |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Val | Phe | Glu | Arg | Leu | Ala | Asp | Lys | Ser | Gly | Lys | Gln | Tyr | Val | Ser | Val |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| Ser | Met | Val | Tyr | Gln | Thr | Leu | Glu | Gln | Leu | Arg | Ser | Gln | Thr | Pro | Leu |
|-----|-----|-----|-----|-----|-----|-----|-----|-----|-----|-----|-----|-----|-----|-----|-----|
|     |     |     | 355 |     |     |     |     | 360 |     |     |     |     | 365 |     |     |

| Ser | Leu | Asn | Gln | Pro | Pro | Gly | Ser | Val | Gln | Leu | Lys | Ile | Pro | Gly | Cys |
|-----|-----|-----|-----|-----|-----|-----|-----|-----|-----|-----|-----|-----|-----|-----|-----|

-continued

```
            370                 375                 380
Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```